US012112842B2

(12) United States Patent
Mougiakakou et al.

(10) Patent No.: US 12,112,842 B2
(45) Date of Patent: *Oct. 8, 2024

(54) SYSTEM AND METHOD FOR IMPROVING THE DRUG THERAPY MANAGEMENT

(71) Applicants: UNIVERSITÄT BERN, Bern (CH); DEBIOTECH S.A., Lausanne (CH)

(72) Inventors: Stavroula Mougiakakou, Bern (CH); Qingnan Sun, Bern (CH); Marko Jankovic, Bern (CH); Laurent-Dominique Piveteau, Lausanne (CH); Stephan Proennecke, Lausanne (CH); João Budzinski, Lausanne (CH)

(73) Assignees: UNIVERSITAT BERN, Bern (CH); DEBIOTECH S.A., Lausanne (CH)

( * ) Notice: Subject to any disclaimer, the term of this patent is extended or adjusted under 35 U.S.C. 154(b) by 416 days.

This patent is subject to a terminal disclaimer.

(21) Appl. No.: 17/670,967

(22) Filed: Feb. 14, 2022

(65) Prior Publication Data

US 2022/0254473 A1 Aug. 11, 2022

Related U.S. Application Data

(63) Continuation of application No. 16/494,753, filed as application No. PCT/IB2018/051769 on Mar. 16, 2018, now Pat. No. 11,430,557.

(30) Foreign Application Priority Data

Mar. 17, 2017 (WO) .................. PCT/IB2017/051571

(51) Int. Cl.
*G16H 20/17* (2018.01)
*A61M 5/142* (2006.01)
(Continued)

(52) U.S. Cl.
CPC ........ *G16H 20/17* (2018.01); *A61M 5/14216* (2013.01); *A61M 5/14248* (2013.01);
(Continued)

(58) Field of Classification Search
None
See application file for complete search history.

(56) References Cited

U.S. PATENT DOCUMENTS 6,656,114 B1 12/2003 Poulsen et al.
7,941,200 B2 5/2011 Weinert et al.
(Continued)

FOREIGN PATENT DOCUMENTS

JP 2002-175372 A 6/2002
JP 2005-215923 A 8/2005
(Continued)

OTHER PUBLICATIONS

Notification of the patentability examination results dated Mar. 25, 2022, issued in Russian Federation Patent Application No. 2019130910/14(060727), 11 pages.
(Continued)

*Primary Examiner* — Manuel A Mendez
(74) *Attorney, Agent, or Firm* — Nixon & Vanderhye P.C.

(57) ABSTRACT

An aspect of the invention provides a method and a product for determining a modification of the therapy management by using a processor unit which retrieves few data related to the blood glucose measurement performed over a predetermined time period; retrieve the medication delivery parameter executed by the delivery device over said predetermined time period; retrieve from the memory data associated to the CIR of the patient; and determine a modification to the therapy based on at least a part of the retrieved data.

20 Claims, 18 Drawing Sheets

(51) Int. Cl.
  *A61M 5/168* (2006.01)
  *A61M 5/172* (2006.01)
  *G16H 40/63* (2018.01)

(52) U.S. Cl.
  CPC ...... *A61M 5/16831* (2013.01); *A61M 5/1723* (2013.01); *G16H 40/63* (2018.01); *A61M 2005/14268* (2013.01); *A61M 2005/16868* (2013.01); *A61M 2202/07* (2013.01); *A61M 2205/18* (2013.01); *A61M 2205/3592* (2013.01); *A61M 2205/50* (2013.01); *A61M 2205/502* (2013.01); *A61M 2205/52* (2013.01); *A61M 2205/8206* (2013.01); *A61M 2230/201* (2013.01)

(56) References Cited

U.S. PATENT DOCUMENTS

| 11,430,557 B2* | 8/2022 | Mougiakakou ... A61M 5/14216 |
|---|---|---|
| 2005/0022274 A1 | 1/2005 | Campbell et al. |
| 2005/0192557 A1 | 9/2005 | Brauker et al. |
| 2006/0272652 A1 | 12/2006 | Stocker et al. |
| 2008/0269585 A1 | 10/2008 | Ginsberg |
| 2010/0185181 A1 | 7/2010 | Alme et al. |
| 2013/0096530 A1 | 4/2013 | Budiman |
| 2014/0009876 A1 | 1/2014 | Wang |
| 2014/0121634 A1 | 5/2014 | Thomson |
| 2015/0190098 A1 | 7/2015 | Patek et al. |
| 2016/0175520 A1 | 6/2016 | Palerm et al. |
| 2016/0260024 A1 | 9/2016 | Campos et al. |
| 2017/0053100 A1 | 2/2017 | Neftel |

FOREIGN PATENT DOCUMENTS

| RU | 2014111290 A | 10/2015 |
|---|---|---|
| WO | 2007/113708 A1 | 10/2007 |
| WO | 2014/009876 A2 | 1/2014 |

OTHER PUBLICATIONS

Notification of the patentability examination results dated Oct. 14, 2021, issued in Russian Federation Application No. 2019130910/14(060727), 5 pages.

Notice of Reasons for Rejection dated Nov. 22, 2021, issued in Japan Patent Application No. JP-A-2019-551280, 8 pages.

Examination Report No. 2 dated Dec. 12, 2023, issued in Australia Patent Application No. 2018235368, 7 pages.

First Office Action dated Mar. 29, 2023, issued in China Application No. 201880018618.7 and English translation, 52 pages.

* cited by examiner

| BG levels mg/dL (mmol/L) | OL | Algorithm |
|---|---|---|
| Adults | | |
| 70 - 180   (3.9 - 10) | 92.55 | 96.45 |
| 50 - 70    (2.8 - 3.9) | 0.00 | 0.00 |
| < 50       (< 2.8) | 0.00 | 0.00 |
| 180 - 300 (10 - 16.7) | 7.45 | 3.55 |
| > 300      (> 16.7) | 0.00 | 0.00 |
| Adolescents | | |
| 70 - 180   (3.9 - 10) | 79.48 | 87.06 |
| 50 - 70    (2.8 - 3.9) | 0.20 | 0.19 |
| < 50       (< 2.8) | 0.03 | 0.00 |
| 180 - 300 (10 - 16.7) | 20.20 | 12.74 |
| > 300      (> 16.7) | 0.09 | 0.00 |
| Children | | |
| 70 - 180   (3.9 - 10) | 74.07 | 89.22 |
| 50 - 70    (2.8 - 3.9) | 0.02 | 0.62 |
| < 50       (< 2.8) | 0.00 | 0.00 |
| 180 - 300 (10 - 16.7) | 25.91 | 10.16 |
| > 300      (> 16.7) | 0.00 | 0.00 |

Table 1

SYSTEM AND METHOD FOR IMPROVING THE DRUG THERAPY MANAGEMENT

CROSS-REFERENCE TO RELATED APPLICATIONS

This application is a continuation application of U.S. patent application Ser. No. 16/494,753 filed Sep. 16, 2019, which is the U.S. national phase of International Application No. PCT/IB2018/051769 filed Mar. 16, 2018, which designated the U.S. and claims priority to International Application No. PCT/IB2017/051571 filed Mar. 17, 2017, the entire contents of each of which are hereby incorporated herein by reference.

FIELD OF INVENTION

Methods, systems and devices adapted for medical infusion of therapeutic fluids to a patient are described herein. For example, a system comprising a module configured to improve "day after day" the drug therapy management, such as the insulin therapy management (a day being an example of time duration of a time period).

STATE OF THE ART

Diabetes is a chronic metabolic disorder which is caused by either the failure of the body to produce insulin (Type 1 Diabetes—T1D) or the inability of the body to respond adequately to circulating insulin (Type 2 Diabetes—T2D). Diabetes is related to severe short-term and long-term complications rendering its effective treatment crucial and urgent.

The main goal in treating diabetes is to avoid hyper- and hypoglycemia in everyday life, in order to reduce the risk of both short- and long-term complications. To this aim, clinicians strive for near-normal glycemia, which is translated as glucose concentration within an upper and lower bound, with as little glucose variability as possible. Treatment of T1D and T2D differs mainly due to the tight dependence of the former to regular insulin administration. T2D is usually treated with a combination of diet, exercise and medical support, such as sulfonylureas, while external insulin is necessary in advanced stages of the disease. On the other hand, T1D is treated with external insulin administration on a daily basis. Today, various technical devices for glucose monitoring and insulin administration are assisting patients and diabetes specialists in optimizing diabetes control.

In order to maintain their Blood Glucose (BG) levels, diabetic patients need to measure/monitor glucose concentration on a regular basis. The first and until now most commonly used method for glucose measurement is via Self-Monitoring of Blood Glucose (SMBG) (also called Blood Glucose Meters (BGM)) which use a drop of whole blood mainly from penetration of the finger (the procedure is performed manually). In recent years, the development of Continuous Glucose Monitoring (CGM) has permitted the measurement, in the interstitial tissue, of glucose continuously with sampling frequencies that now reach one measurement per minute.

Insulin therapy tries to mimic the normal pancreatic response to the variation of glucose concentration in the blood. This concentration may vary slowly depending on the time of the day (e.g. it will be lower at the end of the night than in the evening) and much faster after ingestion of carbohydrates by the patient or when exercising.

Insulin can be (nearly) continuously infused using Continuous Subcutaneous Insulin Infusion (CSII) pumps (i.e. by small increments of a few microliters depending on the accuracy of the device used). This approach uses a pump which infuses insulin 24 hours a day through a catheter placed under the skin, in order to mimic the behavior of the pancreas. The insulin doses are separated into: Basal rates and Bolus doses. Most of the therapy solutions based on CSII request that the patient programs the insulin pump. But, even if the use of a CSII is easy, the therapy management is very tricky, requires extensive training, while errors leading to sometimes dramatic outcomes are common.

Concerning the basal rate, one or several basal rates may be proposed by a caregiver, while some pumps offer several programmable profiles of basal rate, which corresponds to the different type of rhythms that the patient can adopt during her/his daily life. For example, a patient will set a profile for a working day, a week-end day and for the female patients, the menstruation periods . . . . The patient must define the basal rate profiles, which sets the 24 hours injection rates, and the bolus quantities. Nevertheless, the determination of a daily basal rate profile is a complex process.

Concerning the bolus, the patient shall define the bolus quantity dose depending on the meals or correction needs. The patient shall become an expert to evaluate the carbs (carbohydrates) quantity in the coming meal, and to convert it into an insulin quantity. Most of the pumps offer tools to facilitate this evaluation, but there are still many foreseeable errors.

To compensate the potential errors of therapy management, the patient is invited to do regular BG measurements and compensate bad BG levels by infusing a bolus (in case of hyperglycemia) or eating carbs (in case of hypoglycemia).

The programing of the pump becomes even more difficult when an unexpected or uncommon event occurs. For example: occlusion of the infusion pump, physical activity, illness, deviation of the insulin delivery or error in the input data. Since these types of events may reduce or increase the needed quantity of insulin, the therapy management shall take them into account and adjust the basal rate to compensate their effects in glucose control.

Due to the apparition of CGM, a new focus of market development in recent years has been closed loop systems. Very few products are however available today and the features they offer are still very rudimentary. The purpose of a closed loop system is to mimic, as closely as possible the pancreas and therefore create a sort of artificial pancreas (AP). The patient carries with her/him a CGM and an insulin infusion pump. The BG is measured continuously, automatically, and its level is analyzed by a software that adjusts in real time the amount of insulin. Theoretically, the system is supposed to operate completely autonomously, replacing the deficient pancreas, but the prior art systems comprise several drawbacks as described below.

AP is currently in the forefront of research for diabetes, however, the concept was born in the early 70's with the development of Biostator, the first closed-loop algorithm for continuous insulin infusion. To date, research is investigating improved or new technologies for the CGMs and pumps, in order to reduce the inaccuracies and delays in subcutaneous glucose measurement, the delays in subcutaneous insulin absorption and the increase of the CGMs' and pumps' life-time. On the algorithmic side, the interest focuses on the design and development of more sophisticated controllers. Towards this direction, a large variety of algorithms has been proposed in the literature and a series of clinical evaluations is in progress, in order to assess the actual applicability of the proposed methods. Recently, the necessity of a safety mechanism functioning alongside the control algorithm has been addressed, coming as a feedback from the clinical evaluation procedures. Various algorithms based on near-future glucose prediction have been proposed for the early recognition and detection of abnormal metabolic events aiming primarily to the prevention of severe hypoglycemia due to excessive insulin infusion. The control algorithm and the safety mechanism together form a control system, which closes the loop between the CGM and CSII pump. The diagram of such a control system with the interaction of a control algorithm and a safety mechanism is shown in the FIG. 2.

Various control algorithms have been proposed for closing the loop in an AP. Control algorithms for an AP are usually evaluated for their ability to keep glucose within the target range of 70-180 mg/dL which has been commonly accepted as a safe range against both hypo- and hyperglycemia given the measurement errors of the CGM devices.

The AP meets a number of challenges:

Patient safety: Insulin is a very potent drug and any over- or under-delivery may lead to very serious conditions of the patients, even in certain circumstances to death. In the case of over-delivery, the patient will first go into a coma, a condition where she is no more able to react, and, if no change is brought to her therapy, she will die. It is therefore necessary to guarantee that any closed-loop system, and in particular the algorithm that drives it, is able to avoid such situations and to react when it faces them. The different challenges mentioned below give an idea of the path that still lies ahead of an AP.

Glucose measurement errors and delays: The technologies developed today for the external performance of glucose measurement suffer from significant limitations. In principle, with the available resources, the only signal that can be measured in real-time, continuously with low cost and offering good convenience to the patient is glucose concentration in the interstitial fluids through CGMs. Thus, the measured glucose concentration is delayed 12 to 20 minutes compared to the effective concentration in the blood. In some equipment, regular calibration of the CGM is also required by using blood samples, a process highly subjected to the variability of the user's physiology. Despite the cumbersome procedure, the accuracy of the currently available CGM remains relatively poor. Another source of inaccuracy is related to the ability of the sensor to interact only with glucose and avoid other metabolites, a problem termed as sensor selectivity. Furthermore, to date, CGMs life-time is rather short—up to seven days—due to a variety of failures related to degradation, dropouts and battery discharge.

Insulin infusion time-delays: Glucose regulation is attempted only with insulin infusion, which always reacts with some delay (of the order of half an hour for the so-called rapid acting insulins). Furthermore, since insulin can only reduce glucose, compensation of low glucose concentrations using one-sided insulin control renders the process much more cumbersome. Thus, the ability for acute response against out-of-range situations such as hypoglycemia is limited or even restricted.

Inter-patient variability: The high inter-individual variability of the diabetic population is translated in significantly different insulin treatment needs per person in terms of daily insulin dosing and schemes. This variability is related to both physiological differences among individuals and lifestyle variations. Physiological differences include body weight, age, insulin sensitivity and other non-determined factors. Further variation among individuals includes differences in insulin and carbs absorption rate.

Intra-patient variability: Even within the same person, intra-individual variability is significant both in short-term and long-term periods. Short-term changes are mainly related to changes in insulin sensitivity either physiologically during the day (e.g. the dawn phenomenon) or due to physical activity, stress or other non-determined factors. Long-term variations may be attributed to more permanent changes in body weight change, age, lifestyle etc. Inter- and intra-individual variability plays a crucial role in the glucose regulation process and enhances the need for personalized treatment.

System disturbances: Meal carbs content constitutes the main source of external glucose change, and thus, the main disturbance of the glucoregulatory system. Almost half the daily insulin dose is directed to meal carbs content and avoidance of postprandial hyperglycemia. Due to the glucose measurement and insulin action delays, advance knowledge of meal carbs content and meal timing is important for prompt and accurate insulin administration. Erroneous carbs counting is very common and physical activity is another important factor tightly associated both to the glycemic profile and insulin sensitivity (SI). The glucoregulatory system may be affected by a number of additional disturbances which are not known or have unknown/ partially known effects such as stress and illness. As long as there is no grounded information on how these factors interact with the glucose profile, they are classified as uncertainties of the system.

Thus, a closed-loop system can be interpreted as a system of coupled oscillators (FIG. 3). The goal of the algorithms is to define the coupling constant "k" between both oscillators versus the patient data and the CGM input. The position of mass m1 corresponds to the BG values measured by the CGM and position of mass m2 corresponds to the infusion rate of insulin programmed on the pump. The laws of physics show that such systems can be unstable for some intervals of values of m1, l1, m2, l2, k and the initial conditions of the system. These instabilities are mainly due to the values of constant "k", which can put the system in a resonance mode for given values of m1, l1, m2 and l2. In particular, the resonance frequencies depend on lengths l1 et l2 that are intrinsically linked to the accuracies of the CGM measurements and of the insulin delivery. The arger those lengths are, the larger the oscillations are in the resonance modes, and the larger the amplitude of oscillation is, the higher is the risk of having a fatal hypoglycemia.

In conclusion, the systems of the prior art have several drawbacks and still face important challenges in realizing their full potential. For example, its algorithms are very complex and effective only for stable patients and more quiet periods of the day—at night. They do not have the same effectiveness for unstable patients or less predictable periods of the day (such as for example either meals or periods of intense activity or significant unexpected changes of rhythm during the daily life of the patient).

Furthermore, the current closed loop systems have to be used only with a CGM because their algorithms need the input of continuous measures of the blood glucose level of the patient, and cannot be used with BGM. Indeed, in usual case, less than ten or eight (sometimes only five) glucose level data points are provided per day with a BGM, and the prior art systems do not have enough data for allowing it to converge and predict any potential need in insulin.

GENERAL DESCRIPTION OF THE INVENTION

The present invention intends to overcome drawbacks of the prior art systems, as outlined above. The present invention intends to be an improvement to a system for managing diabetes, for example to be an improvement to a controller for determining medication delivery parameter(s) and/or a factor required to compute an insulin delivery amount.

From a conceptual standpoint, one of a plurality of goals is not to focus on a microscopic view (for example the continuous measurements of the BG). For example, an aspect of the invention proposes to take into account (only) data relevant of a first time period which is preferentially a long time period (for example 12-24 h or more) so as to have an overview of the therapy. The proposed solution may define the basal rate and/or the carbohydrates to insulin ratio (CIR) based on BG measurements via preferentially a SMBG and other optional relevant data which may be used for a subsequent time period. Furthermore, the system may be configured to improve the therapy management over time based on past data, for example, the basal rate profile of the previous days or the extreme of the basal rate, for example since the initiation phase (described thereafter). And, this system may not require a CGM system and it may be applicable for type 1 and/or type 2 diabetics. Thus, the system may be configured to improve the management of diabetes independently of the type of glucose monitoring device used which represents a genuine revolution for the diabetes management and the patient life. One of the primary reasons is that SMBG is the most commonly used glucose monitoring device for the diabetes patients. Indeed, the majority of the individuals with diabetes under insulin treatment (Type 1 and Type 2) are using SMBG rather than CGM, since CGMs and replacement sensors are much more expensive than SMBG. Furthermore, in most countries CGM is either not available or not covered by health insurances (or just for a limited number of patients).

Thus, the system may be adapted to determine a therapy modification based on:
  glucose data episodically received by the system, and/or
  discrete measurement of body fluid analyte relating to the patient glucose, and/or
  discrete data provided for example by a Self-Monitoring Blood Glucose, and/or
  other data,
which would not be possible with the prior art devices because they require frequent and/or continuous measurements.

The present invention solves the above problems by providing, according to a first aspect of the invention, a method of adapting a therapy to a patient, the method comprising the steps of:
  performing at least two measurements of a body fluid analyte of the patient with a Self-Monitoring Blood Glucose over a first time period;
  retrieving from a memory device at least one of:
    a medication delivery parameter executed over the first time period, including at least one of a basal rate and a bolus; and
    a CIR of the patient; and
  determining, by a processor unit, a therapy modification by taking into account the at least two measurements and the retrieved data; preferentially, the therapy modification may comprise at least one of a modification to the basal rate and a modification to the CIR.

The method further comprises at least one of the following steps of:
  displaying at least a part of therapy modification;
  suggesting to the patient the therapy modification; and/or delivering insulin amount by taking into account the therapy modification for a subsequent time period.

In comparison with the systems of the prior art, in particular the closed loop system, the "time period" according to an aspect of the invention is preferentially longer than the time period used by the closed loop systems using a CGM. For example, the time duration of the first time period may be comprised between 1 hour and 36 hours, preferentially between 10 hours and 24 hours or one day. Furthermore, the time duration between two measurements taken into account by the method may be comprised between 1 hour and 4 hours.

This is to have an overview of the therapy thus the processor unit does not focus on the data of a short time period. Further, the processor unit uses just few measurements of the BG level during the time period so that it becomes possible to use a SMBG.

Thus, the method according to an aspect of the invention allows determining a basal rate profile and/or a CIR with only ten or eight or five (or less) measurements of BG of a patient per time period, preferentially per day. In other terms, an aspect of the invention allows determining an insulin therapy by using the BG measurements performed by a BGM and the basal rate of the current time period. This is impossible with the closed loop systems of the prior art because their algorithm needs several measurements per minute. Preferentially, the low number of measurements in the time period just preceding the suggestion of a new basal rate and/or of a new CIR is compensated by the fact that the algorithm may take into account all what it learned from the patient history (for example, the basal rate or CIR of the past time period). To determine the therapy modification, a mathematical model may be used in order to compute or calculate the modified parameter.

In an example embodiment, the processor unit takes into account the data previously amended (basal rate and/or CIR) to determine the new basal rate and/or the new CIR.

Thus, the process unit learns over time.

In an other example embodiment, the process unit learns the usual practices of the patient and takes into account the usual practices of the patient for determining the basal rate or the CIR for the subsequent time period. For example, when a patient tends to overestimate or underestimate the carbs of the meals, the processor unit takes into account this error and thus reduces or increases the basal rate or the CIR.

In a second aspect, the present invention solves the above problems by providing a system for diabetes management of a patient which comprises:
  an input device (also called acquisition device) configured for receiving glucose data relating to a glucose level of the patient;
  a delivery device configured for delivering insulin to the patient according to a medication delivery parameter including at least one of a basal rate and a bolus;
  a memory device configured to store
    at least one glucose data and
    at least one of the medication delivery parameter and a CIR relating to the Carbohydrate to Insulin Ratio information of the patient;

computer-executable instructions which, when they are executed are adapted to:
retrieve from the memory device at least two glucose data over a first time period;
retrieve from the memory device at least one of:
the medication delivery parameter executed by the delivery device over the first time period; and
the CIR; and
determine based on at least a part of the retrieved data a therapy modification comprising a modification of at least one of:
the basal rate; and
the CIR.

The therapy modification is preferentially intended to be used for a subsequent time period by the delivery device; and the glucose data are preferentially provided by a Self-Monitoring Blood Glucose.

The computer-executable instructions may be further adapted to:
display at least a part of therapy modification;
suggest to the patient the therapy modification; and/or
control the delivery device to deliver an insulin amount by taking into account the therapy modification for a subsequent time period.

A tuning module of the system is implemented as software or hardware, which for example comprises a processor unit configured to execute the instructions described above. The tuning module may be arranged or located in the delivery device or a remote control device or in a remote server or cloud.

One of the huge advantages of this solution is that it provides an AP algorithm based on SMBG measurements, which can be used by both type 1 and type 2 diabetics.

According to a third aspect, the invention solves the above problems by providing a system and a method adapted for adapting diabetes management of a patient independently of the type of glucose monitoring device used.

The method comprises the steps of:
obtaining at least two measurements of glucose level of the patient performed over a first time period;
obtaining at least one of:
a medication delivery parameter executed over the first time period, including at least one of a basal rate and a bolus; and/or
a CIR of the patient for example used for calculating a bolus during the first time period; and
determining or calculating a medication delivery parameter and/or a CIR which is intended to be used for a subsequent time period, by taking into account the obtained data.

In a preferred embodiment, the step of "determining or calculating" is performed independently of the device used to measure the blood glucose concentration. This device may be a SMBG, a CGM or any other device configured to measure, automatically or manually, the blood glucose concentration A goal of this method is the determination of an insulin therapy independently of the type of glucose monitoring device (for example SMBG or CGM) for a subsequent time period.

In a further aspect, the invention relates to a computer program product loadable into an internal memory of a digital computer comprising software code portions for performing the method disclosed above when said product is run on a computer.

In a further aspect, the invention relates to a computer program product which comprises a non-transitory computer useable medium having a computer program logic for enabling at least one processor in a computer system to determine a medication delivery parameter and/or CIR independently of the type of glucose monitoring device used between a SMBG and a CGM. The computer program logic comprises the steps of:
obtaining at least two measurements of glucose level of the patient performed over a first time period;
obtaining at least one of:
a medication delivery parameter executed over the first time period, including at least one of a basal rate and a bolus; and/or
a CIR of the patient for example used for calculating a bolus during the first time period; and
determining or calculating a medication delivery parameter and/or a CIR which may be used for a subsequent time period, by taking into account the obtained data.

According to a fourth aspect of the invention, this advanced technology allows to obtain a system and a method adapted for monitoring a closed loop device. In this case, the method comprises the steps of:
obtaining at least two measurements of glucose level of the patient performed over a first time period;
obtaining at least one of:
a medication delivery parameter executed over the first time period, including at least one of a basal rate and a bolus; and/or
a CIR of the patient for example used for calculating a bolus during the first time period;
determining or calculating a set of acceptable data comprising for example at least one of a basal rate and/or a CIR which may be used for a subsequent time period, by taking into account the obtained data; and
comparing the set of acceptable data to the data computed by the closed loop device for a subsequent time period; or
comparing the set of acceptable data to the medication delivery parameter (or CIR) intended to be used for a subsequent time period.

If the difference is greater than a threshold, the method further comprises the step of alerting the patient or a user (such as a doctor or a nurse, . . . ) or suggesting an other medication delivery parameter in compliance with said acceptable range.

Any of the following limits may further apply:
absolute limits defined by the HCP (e.g., 25 U for bolus, 10 U/h for basal), and/or
IOB limit, and/or
maximum change of therapy of 10%, and/or
other limits using a predictive models, as described in this document.

In a preferred embodiment, the system comprises:
an acquisition device configured to acquire a plurality of glucose data of the patient;
a closed loop device configured to determine a medication delivery parameter including at least one of a basal rate and a bolus;
a memory device configured to store a plurality of data relating for example to the medication delivery parameter and/or to glucose data;
a delivery device configured to deliver a drug to a patient according to the medication delivery parameter; and
a processor programmed to:
receive blood glucose data of the patient measured over a predefined time period;
receive the medication delivery parameter applied by the delivery device over said predefined time period;

determine or calculate a set of acceptable data comprising for example at least one of a basal rate and/or a CIR which may be used for a subsequent time period, by taking into account the received data.

In a preferred embodiment, the processor is further programmed to:

receive the medication delivery parameter (and/or CIR) computed by the closed loop device (or intended to be used) for the subsequent time period; and compare the set of acceptable data to the medication delivery parameter (and/or CIR) computed by the closed loop device (or intended to be used) for the subsequent time period.

If the difference reaches a predetermined threshold, the processor is programmed to:

alert the patient or other user, and/or suggest an other medication delivery parameter in compliance with said acceptable range, and/or stop the closed loop device.

In a preferred embodiment, the processor uses an algorithm or program or software or computer-executable instructions which is different from the algorithm or program or software or computer-executable instructions used by the closed loop device. The closed loop device comprises a processor which is different from the processor used for the monitoring process. Furthermore, in a preferred embodiment, the processor used for the monitoring process is use as a watch dog.

LIST OF FIGURES

The invention will be better understood at the light of the following detailed description which contains non-limiting examples illustrated by the following figures.

Figure 1A:
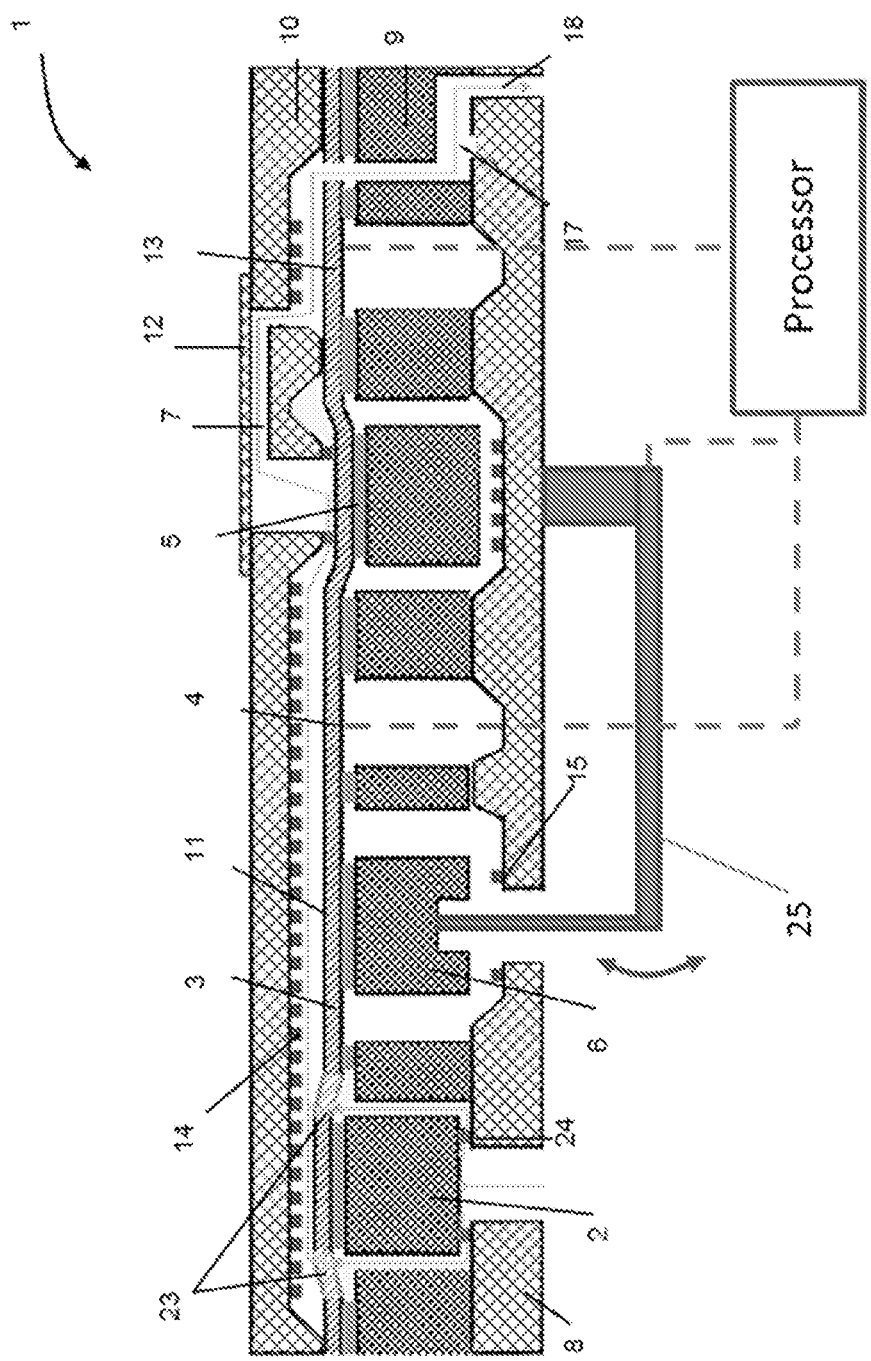
FIGS. 1a, 1b, 1c, 1d and 1e show different views of an example system according to the invention.

FIGS. 12, 13, 14, 15, 16, 17a, and 17b illustrate examples of the flowchart according to an aspect of the invention.

Table 1 shows primary in silico evaluation results of an use example in terms of glucose levels

LIST OF ELEMENTS

1 Pump
2 Inlet valve
3 Pumping membrane
4 Sensor membrane
5 Outlet valve
6 Mesa
7, 17 Channel
8 Base plate
9 Second plate
10 Top plate
11 Pumping chamber
12 Cover
13 Sensor membrane
14, 15, 24 anti-bonding layers
18 Outlet
23 Arm of the valve
25 Actuator
100 Pumping device
101 Disposable part
102 Non-disposable part
103 Reservoir
104 Housing
105 Vent
106 Electronic elements
107 Housing
108 Vent
109 Battery
110 Patch
111 Infusion set
112 Housing
113 Inlet port of the infusion set
114 Outlet port of the pumping device
115 Cannula
200 Remote controller
201 Screen
202 Button
203 Telecommunication device
300 System
301 Processor
302 Memory device
303 Input device
304 Glucose sensor
305 Delivery device
306 Display device (or GUI)
307 Closed loop device

DETAILED DESCRIPTION OF PREFERRED EMBODIMENTS OF THE INVENTION

In the following detailed description, reference is made to the accompanying drawings that form a part hereof, and in which are shown by way of illustration several embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, any direction referred to herein, such as "top", "bottom", "left", "right", "upper", "lower", and other directions or orientations are described herein for clarity in reference to the figures and are not intended to be limiting of an actual device or system. Devices and systems described herein may be used in a number of directions and orientations.

As used herein, "have", "having", "include", "including", "comprise", "comprising" or the like are used in their open ended sense, and generally mean "including, but not limited to.

As used in this specification and the appended claims, the term "or" is generally employed in its sense including "and/or" unless the content clearly dictates otherwise.

The term "substantially" as used herein, is a broad term and is used in its ordinary sense, including, without limitation, being largely but not necessarily wholly that which is specified.

The term "microprocessor" and "processor" as used herein, is a broad term and is used in its ordinary sense, refers without limitation to a computer system or processor designed to perform arithmetic and logic operations using logic circuitry that responds to and processes the basic instructions that drive a computer.

The term "ROM" as used herein, is a broad term and is used in its ordinary sense, refers without limitation to read-only memory, which is a type of data storage device manufactured with fixed contents. ROM is broad enough to include EEPROM, for example, which is electrically erasable programmable read-only memory (ROM).

The term "RAM" as used herein, is a broad term and is used in its ordinary sense, refers without limitation to a data storage device for which the order of access to different locations does not affect the speed of access. RAM is broad enough to include SRAM, for example, which is static random access memory that retains data bits in its memory as long as power is being supplied.

The term "RF transceiver" or "wireless communication device" as used herein, is a broad term and is used in its ordinary sense, refers without limitation to a radio frequency transmitter and/or receiver for transmitting and/or receiving signals.

The terms "connected" and "operably linked" as used herein, is a broad term and is used in its ordinary sense, refers without limitation to one or more components being linked to another component(s) in a manner that allows transmission of signals between the components.

The term "algorithm" as used herein, is a broad term and is used in its ordinary sense, refers without limitation to the computational processes (for example, programs) involved in transforming information from one state to another, for example using computer processing.

The term "alarm" as used herein, is a broad term and is used in its ordinary sense, refers without limitation to audible, visual, or tactile signal that are triggered in response to detection of an anomaly.

The term "computer" as used herein, is a broad term and is used in its ordinary sense, refers without limitation to machine that can be programmed to manipulate data.

The term "patient" as used herein, is a broad term and is used in its ordinary sense, refers without limitation to any individual from whom information is collected or any individual receiving a treatment.

The term "caregiver" as used herein, is a broad term and is used in its ordinary sense, refers without limitation to nurses, doctors, and other health care provider staff.

The term "glucose monitoring device" as used herein, is a broad term and is used in its ordinary sense, refers without limitation to device configured or adapted to monitor or measure the glucose concentration of a patient. A glucose monitoring device may be a CGM, a SMBG or other device.

The term "continuous glucose sensor" or "CGM" as used herein, is a broad term and is used in its ordinary sense, refers without limitation to a device configured or adapted to continuously or continually (automatically) measure the glucose concentration of a bodily fluid (e.g., blood, plasma, interstitial fluid, blood-free interstitial fluid and the like), for example, at time intervals ranging from fractions of a second up to, for example, 1, 2, or 5 minutes. It should be understood that continual or continuous glucose sensors can continually measure glucose concentration without requiring user initiation and/or interaction for each measurement. A CGM is different from a SMBG (also called BGM) which is used to get a single blood glucose level value manually.

The term "self-monitoring of blood glucose" or "SMBG" as used herein, is a broad term and is used in its ordinary sense, refers without limitation to a device configured or adapted to be used manually so as to measure the glucose concentration of the patient. A SMBG may be adapted to measure from a drop of blood the patient glucose concentration. A SMBG may be adapted to perform the measurement outside of the patient's body. For example, the general instructions for using a blood glucose meter (SMBG or BGM) comprise several steps manually performed by a user (for example the patient):
1. Wash the hands or clean the finger of the patient or other site with alcohol.
2. Prick the site with a lancing device.
3. Put a little drop of blood on a test strip.
4. Insert the test strip in the blood glucose meter.

Only after these steps, the blood glucose meter determines the blood glucose level and communicates this value to the user.

The term "insulin therapy" as used herein, is a broad term and is used in its ordinary sense, refers without limitation to an amount and/or schedule of the insulin to be delivered to the host (the patient) and/or the data required to compute the amount of an insulin dose.

The term "basal" as used herein, is a broad term and is used in its ordinary sense, refers without limitation to a basal level that is necessary for health or life. For example, in the case of insulin therapy, it may describe a dosage of insulin intended to "cover" the glucose output of the patient metabolism from organs like the liver or the muscles, but not limited to these specific organs.

The term "basal rate" or "basal rate profile" as used herein, is a broad term and is used in its ordinary sense, refers without limitation to a rate or a set of rates of a basal supply of a solution to a patient over a time period. The delivery may be substantially continuous or performed by several pulses (depending on the pumping mechanism or device) in order to obtain a substantially similar effect to a continuous supply. A single basal rate, as used herein, refers without limitation to a single, flat or fixed rate delivered over a determined period of time, for example 1 second, 1 minute, 1 hour or more. A basal rate or a basal rate profile may comprise one or more single basal rates throughout a 24-hour period (for example).

The term "bolus" as used herein, is a broad term and is used in its ordinary sense, refers without limitation to a single dose of insulin, usually given over a short, defined period of time, that has been calculated and/or estimated to be sufficient to cover an expected rise in blood glucose, such as the rise that generally occurs during/after a meal The term "CIR" as used herein, is a broad term and is used in its ordinary sense, refers without limitation to Carbohydrates to Insulin Ratio which is a ratio used to convert a portion of carbohydrates that is contained in a meal to its corresponding quantity of insulin that is needed to absorb those carbohydrates.

The term "CIR profile" as used herein, is a broad term and is used in its ordinary sense, refers without limitation to a ratio or a set of ratio applied for the meals eat over the time period. The CIR profile may comprise one ratio for all meals of the day or a ratio for each meal.

The term "intelligent" as used herein, is a broad term and is used in its ordinary sense, refers without limitation to systems and methods programmed to be able to adjust to changes in the current conditions and make deductions from information being processed.

The term "time period" as used herein, is a broad term and is used in its ordinary sense, refers without limitation to a single point in time and a path (for example, range of time) that extends from a first point in time to a second point in time. For example a time period may be comprised between 1 hour and 36 hours. A time period may be variable or fixed and may be predetermined or not.

The term "measured analyte values" as used herein, is a broad term and is used in its ordinary sense, refers without limitation to an analyte value or set of analyte values for a time period for which analyte data has been measured by an analyte sensor. The term is broad enough to include data from the analyte sensor before or after data processing in the sensor and/or receiver (for example, data smoothing, calibration, or the like).

The terms "programmed" and "programmable" as used herein, is a broad term and is used in its ordinary sense, refers without limitation to be or able to be arranged, as in a series of steps and/or instructions to be carried out, such as by a computer. As used herein, the terms programmed and programmable includes "pre-programmed," "pre-programmable," "re-programmed" and "re-programmable." In one example, a constraint can be programmed prior to use and/or reprogrammed at a later time.

T1D refers to a Type 1 Diabetes mellitus. It is characterized by the destruction through an auto-immune process of the insulin-producing beta cells located in the islets of Langerhans in the pancreas. This leads to the deficiency of insulin supply and therefore to the inability of most cells to uptake glucose as a source of energy. The gold standard treatment for this type of diabetes is insulin infusion. Some recent studies tend to show that the prevalence of this form of the disease is growing slightly faster than the population.

T2D refers to a Type 2 Diabetes mellitus. This form of the disease is due to the arising of insulin resistance or reduced insulin sensitivity by the cells, therefore requiring more efforts of the insulin-producing beta cells in the pancreas. On the long term this may induce a fatigue of these beta cells and potentially reduced insulin secretion. The treatment is predominantly done using pharmaceutical agents that will increase the sensitivity of target organs to insulin (sensitizers like the metformin) or agents that will increase the amount of insulin secreted by the pancreas (secretagogues like the Sulfonylureas or GLP-1 analogs). However, about 30% of T2D patients are treated with insulin.

Use Example

Figure 11:
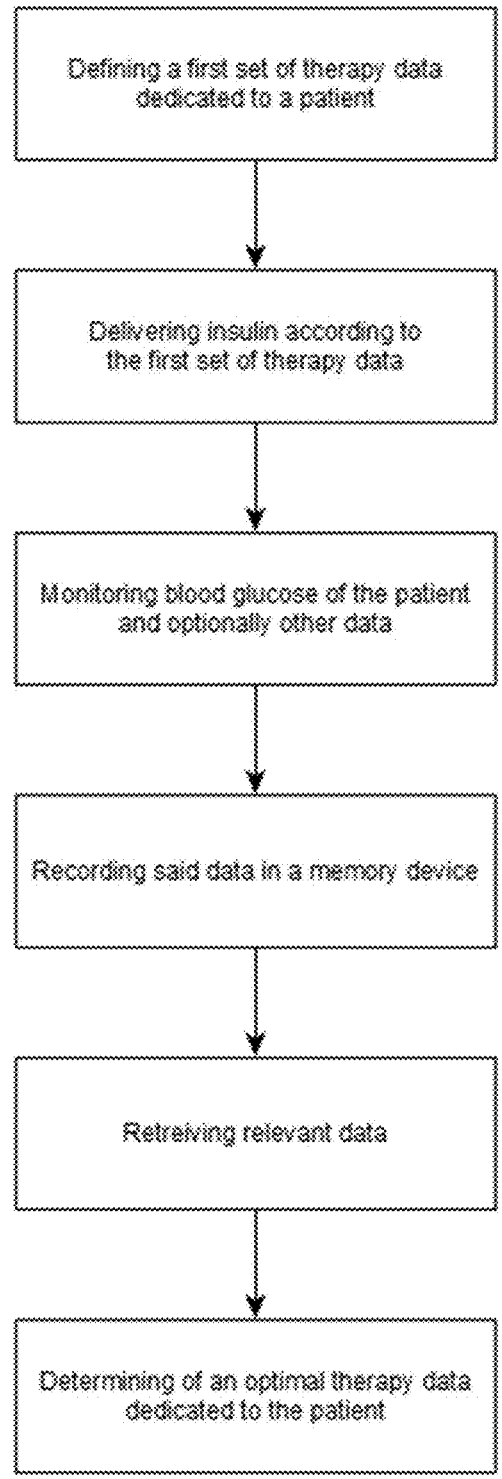
FIG. 11 illustrates an example of an initial phase according to an aspect of the invention.
Figure 12:
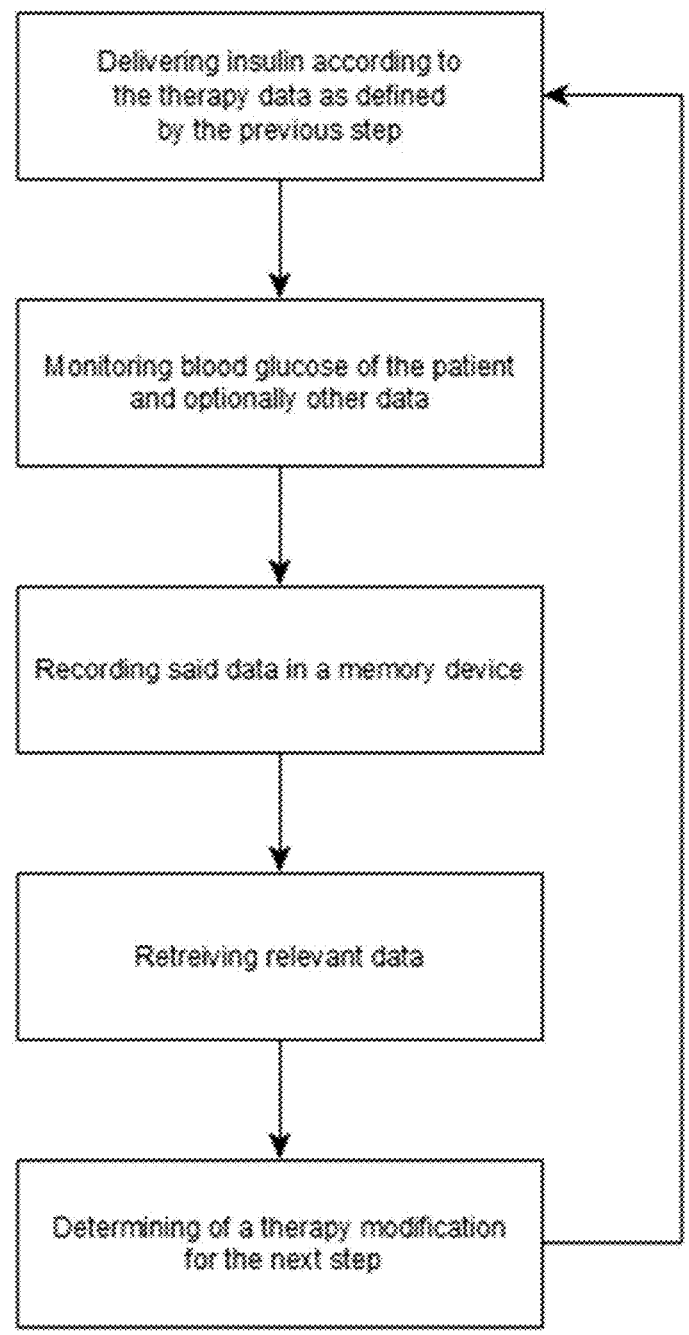

Focus now on the FIG. 11 which shows a flowchart of an optional initial phase. Preferentially, before using a delivery system as described in this document, the patient meets a caregiver or a physician to define a first set of therapy data (for example a basal rate profile and/or one or more CIR, for example a CIR profile). When this first set of therapy data has been defined a first phase (called initialization phase) can start. Preferentially, during this initialization phase, the patient receives normally her/his therapy or she/he may receive her/his therapy in a controlled manner, for example at the hospital. Thus, a determined amount of insulin is delivered to the patient according to the first set of therapy data. For example, a delivery system is programmed with the therapy data predefined by the caregiver (the first set of therapy data) and thus the delivery system delivers the insulin depending of this data first set of therapy data. If necessary, the insulin therapy may be changed by the caregiver or by the patient under the guide of her/his caregiver. Preferentially, during the initialization phase, the system gathers data to initialize its parameters. Thus, the system may offer a personalized optimized therapy from the very beginning of the next phase.

The time duration of the initialization phase may be one day or more days or one week, preferentially between 2 and 15 days, more preferentially between 4 and 7 days. During this phase, as described by the step 4/5 of the FIG. 11, the blood glucose of the patient is monitored, preferentially in a continuous manner. Thus, the patient may wear a CGM to measure or monitor continuously her/his BG level. Other data may be monitored, for example at least one data of the following list: a basal rate used, an amount of insulin effectively delivered to the patient, a patient activity, a food eaten, a patient weight, current patient age, health status of the patient, a BG level, a bolus infused, a carbs of the food eaten by the patient. Furthermore, the system may store in a memory device said data (BG, BR, . . . )

At the end of this phase, a therapy may be determined and may include at least one basal rate and/or at least one CIR. This phase allows the system to learn more quickly and/or to define a first optimal therapy, which is optimal and personalized according to the knowledge acquired during the initialization phase.

The aforementioned first phase (initialization phase) may improve the performance of the AP algorithm, since during the first phase (part of) the parameters of the AP algorithm may be initialized and/or personalized based on the patient specific data. However, the first phase is not a must for using a delivery system as described in this document. The parameters, which should be initialized, may be initialized to 0, 0.5 or other values or in other proper manners. In this case the first phase may be skipped.

After the initialization phase (if an initialization phase is included), a second phase (as shown in the FIG. 12) can start. This phase allows improving the therapy day after day based on the new knowledge acquired during one or more time periods. The patient may no longer use the CGM and she/he may use only a BGM for monitoring her/his BG. The second phase may be performed independently of the type of glucose monitoring device used.

At the beginning during the first time period of the second phase, the delivery system is programmed with the first optimal therapy (for example, the therapy data as defined by the previous step). Thus, for instance, the processor of the system retrieves or reads from a memory (memory of the system or of a remote medical server) the first optimal therapy data and controls the delivery device according to this data over the first time period. In particular, the delivery device delivers insulin according to the basal rate profile of the first optimal therapy. This basal rate profile may comprise one or more single basal rate. And, at the meal time, the processor retrieves or reads from a memory the CIR profile of the first optimal therapy and uses this CIR profile to compute a bolus dose. This CIR profile may comprise one single CIR or several CIR. Specific CIR may be dedicated to a meal type (breakfast, lunch, dinner and snack).

Over the first time period, the system stores the BG measurements performed.

Preferentially, during the first time period, for example near the end of this time period (but not necessary at the end of the time period), the system may use an algorithm to determine a new optimal therapy (for example basal rate profile and/or CIR profile), which may be used for a subsequent time period, for instance the next time period which will start at the end of the first time period. Preferentially, the basal rate profile and/or the CIR profile are computed only once per time period (for example only once per day).

Optionally, the CIR or the CIR profile may not be computed at the same time as the basal rate profile. In this case, the CIR or the CIR profile may be computed at a meal time or just before (for example at the first meal of the current time period or at each meal of the current time period).

It is to be understood that the new optimal therapy is optimal according to the knowledge acquired during one or more time periods for example during a current time period and/or during one or more past time periods and/or during the initialization phase.

Preferentially, in order to determine the new optimal therapy, the processor of the system may take into account at least one data of the following list: blood glucose measurements of the current time period, basal rate of the current time period, basal rate of one or more past time periods, CIR or CIR profile of the current time period and CIR or CIR profile of one or more past time periods.

Optionally, in order to determine the new optimal therapy, the processor of the system may further take into account at least one data of the following list: blood glucose measurements of one or more past time periods, an amount of insulin effectively delivered to the patient, a patient activity, a food eaten, a patient weight, current patient age, health status of the patient, a BG level, a bolus infused, a carbs included in the food eaten by the patient.

Optionally, the new optimal therapy may be limited to a change of at most 20%, or preferentially 10% or less of the old therapy (for safety reasons).

In case where the BG measurements is required to determine the new optimal therapy, the system needs only ten or less blood glucose measurements per time period or per day, preferentially eight or less, more preferentially five or less.

The determination step may be a request launched by the patient. In this case, the system may comprise a "launch" button (for example a virtual button on the touch screen of the remote controller).

The determination step may be launched (for example by the patient) throughout or just after (few seconds after) the last measurement of blood glucose. For instance, when the patient measures her/his BG level for the last time of the current time period, the system may suggest to the patient to launch the determination of the optimal therapy for the next time period. A virtual "launch" button may be activable or enable only after a predetermined measurement (for example only after five measurements over the current time period) or a specific screen may be displayed only after a predetermined measurement (for example the measurement performed at the diner or at the bedtime snacks).

When a new optimal therapy has been computed by the processor, the system may automatically execute the new therapy or may be executed when the subsequent time period will start. Preferentially, the system suggests to the patient the new therapy and the patient accept or not the new therapy for the subsequent time period (for example the time period will start at the end of the current time period). In this case the system acts as a coach and gives the suggestions to the patient.

The system may act as a coach wherein the system does not determine a specific therapy but propose an acceptable range and the patient determine herself her therapy for the next time period. The range may be just a suggestion or binding range.

The system may be used as a safety control or a watchdog of a closed loop device. In this case, the system computes an acceptable range of the therapy and the closed loop device can control the delivery device only in this range. If the closed loop device tries to overcome the range, the system may trigger an alarm or prompt the patient to validate the therapy suggested by the closed loop device.

The time duration of the time period may be comprised between 1 and 36 hours, preferentially between 12 and 30 hours, preferentially substantially equal to 24 hours. A time period may be start between 00:00 and 24:00 of a day, preferentially substantially at 00:00 or after 6:00 or after 20:00. The new time period may start when the new optimal therapy has been computed, in this case the duration of the time period is preferentially variable.

The time period may vary from one individual to another and/or from a time period to another.

The system may be configured for learning the usual practices of the patient and for taking into account the usual practices of the patient for determining the basal rate or the CIR of the subsequent. For example, when a patient tends to over or under-evaluate the carbohydrates comprised in the meal of the patient, the system may take into account this error and thus reduces or increases the basal rate and/or the CIR for the next time period.

Preferentially, after the initialization phase, the system does not use any CGM or the algorithm of the system no longer uses data measured by a CGM for computing an optimal therapy. It is an important improvement because, as described above, the systems using CGM comprise several drawbacks. Considering the system may be used without data measured by a CGM, the system uses a BGM or takes into account only the data measured by a BGM or the algorithm use the data of the BGM to compute the optimal therapy, in other terms, the system is configured to compute an optimal therapy (for example basal rate and/or CIR profile) with only few blood glucose measurements. For example, the blood glucose measurements may be less than or equal to 10 per time period, preferentially between 8 and 3 per time period, more preferentially between 7 and 4 per time period. The blood glucose measurements may be at least 10 minutes apart, preferentially 30 minutes, more preferentially 1 hour or 2 hours and even longer. Thus the system may be used without CGM or the algorithm does not need data measured by a CGM. In other words, after the initialization phase the system does not need a continuous monitoring of the blood glucose level via a CGM.

Example Method According to an Aspect of the Invention

An aspect of the invention discloses a method for providing therapy modification in an infusion system as described below. The method may be executed by a computer readable medium including computer executable instructions such as used with a personal computer, a delivery device, a remote controller of the delivery device or a remote sever. The method comprises the following steps:

retrieving from a memory device at least two measurements of blood glucose of a patient, over a first time period;

retrieving from the memory device a medication delivery parameter executed over said first time period, including at least one of a basal rate and a bolus;

retrieving from the memory device data associated to the CIR of the patient; and determining, by a processor unit, a modification to the basal rate and/or a modification to the CIR The processor unit takes into account at least a part of the retrieved data for determining the new basal rate and/or new CIR. This new data may be stored in the memory device to be used during a subsequent time-period, for example the next time-period.

The modification of the basal rate and/or the modification of the CIR may be determined in order to prevent or to limit the number of hyperglycemia events and/or the number of hypoglycemia events which could occur during the subsequent time period, for example the next time-period.

The processor may compute a rate of change to be applied to the therapy parameters of the first time-period to obtain the new therapy parameters (for example the modified basal rate and/or the modified CIR). This rate of change may take into account several input data as described by the FIG. 15.

The determining step may use an algorithm as disclosed above (in order to compute or calculate the new parameters) and/or use a data table stored in a memory device and/or use a decision tree.

Figure 13:
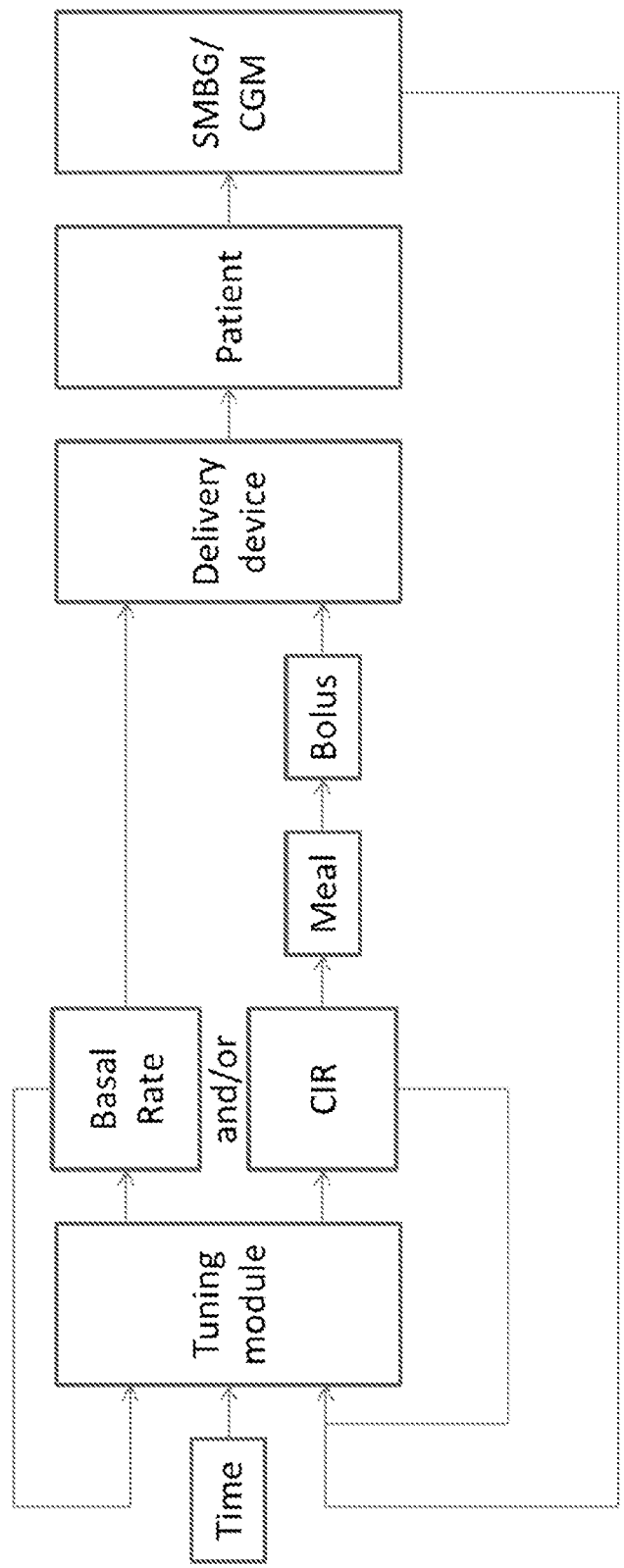

The FIG. 13 illustrates an example of a flowchart. The determining step may be performed by a tuning module which executes computer-executable instructions. To determine the therapy modification, the tuning module may take into account the basal rate, the CIR, the time and glucose measures of the first time-period. The tuning module may compute a modified therapy including at least one of a basal rate and a CIR.

Figure 14:
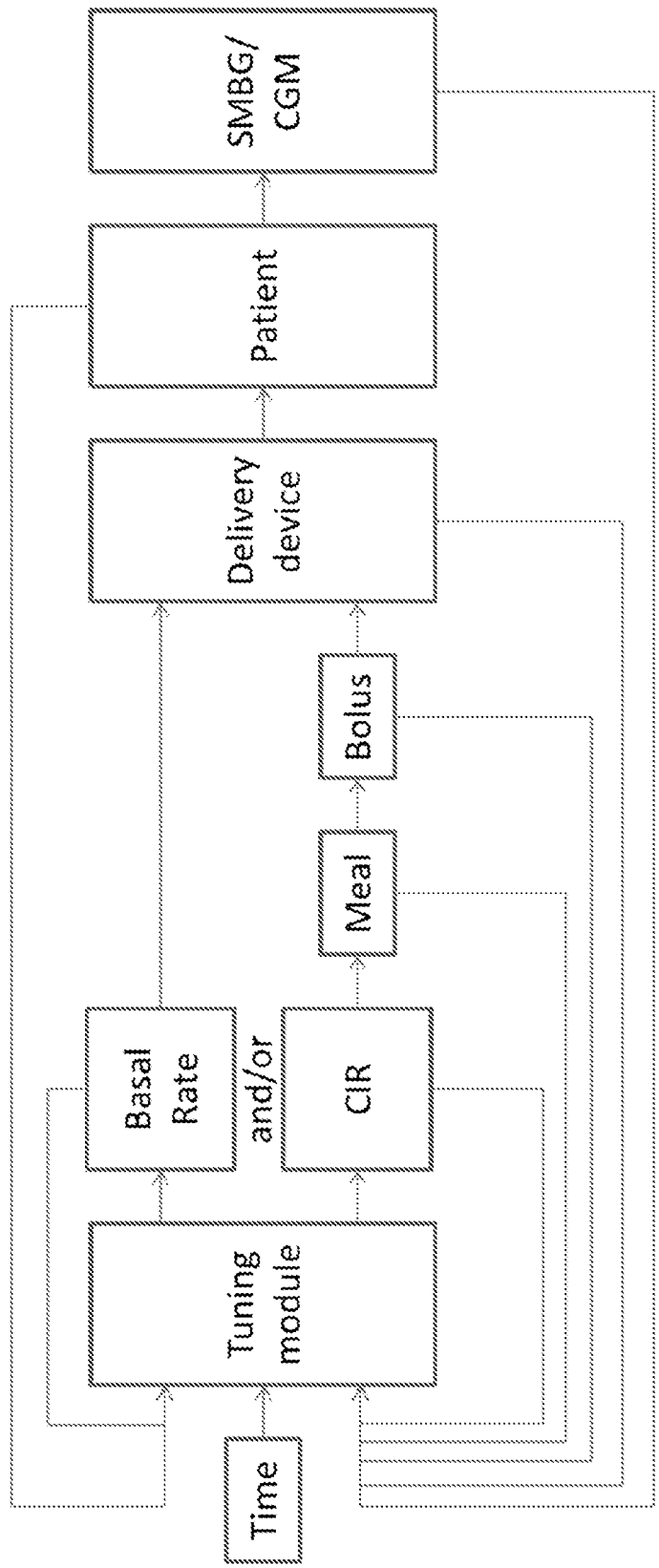

The FIG. 14 illustrates a similar example wherein the tuning module further takes into account at least one data of the following list: a data relating to a meal taken (type of meal, amount of carbohydrate, . . . ), data relating to the bolus infused, a data relating the status of delivery device, a data relating the insulin amount effectively infused to the patient, a data relating to the patient (Insulin on board, age of patient, activity of the patient, . . . ) and other data (type of glucose monitoring device, . . . ).

Figure 15:
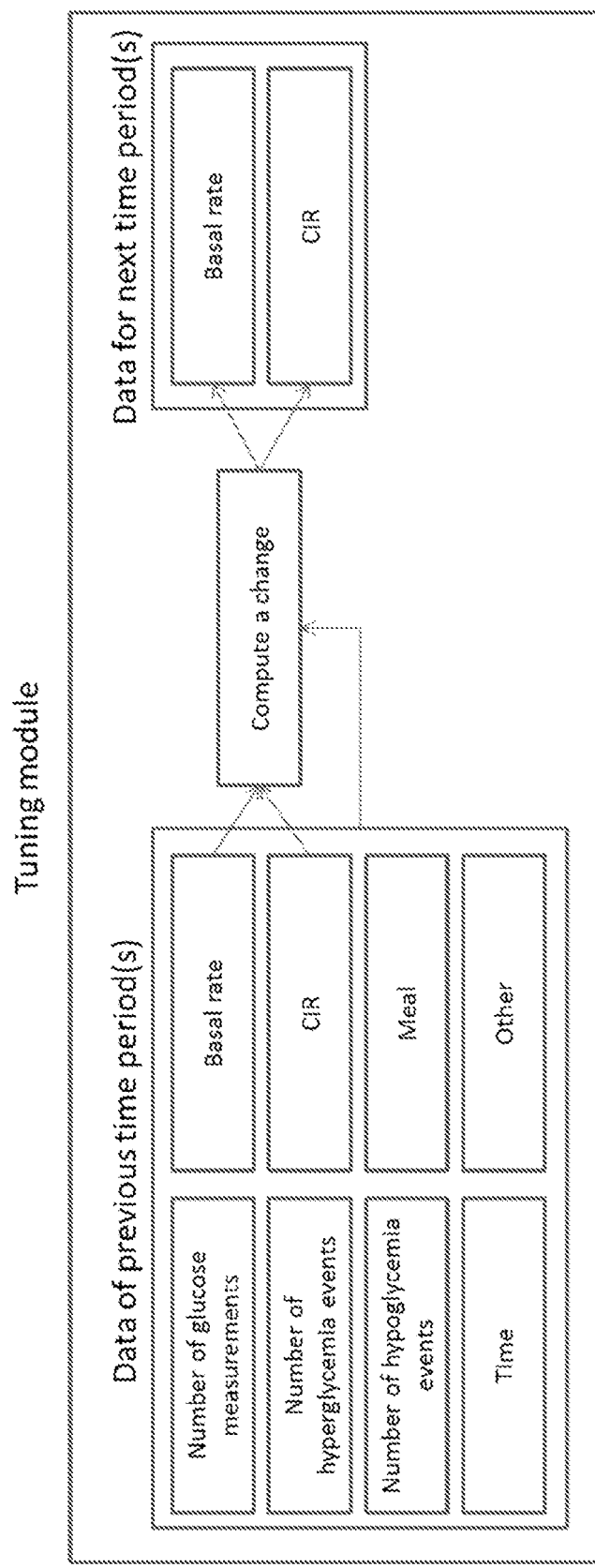

The FIG. 15 schematizes an example of the tuning module. In this example, the tuning module uses the basal rate and/or the CIR of (a) previous time period(s) (which has (have) been executed by the delivery device, for example) to compute a change. This change may be a ratio applied to the previous basal rate and/or CI R in order to obtain the basal rate and the CIR adapted for (a) next time period(s).

The tuning module (or the system) may determine (or compute) the number of available blood glucose measures, the number of hyperglycemia events and/or the number of hypoglycemia events. The tuning module may take into account other data, for example a data relating to the time, a data relating to the meal or other. All or a part of this data may be used to compute the change (for example the ratio to be applied).

Figure 17A:
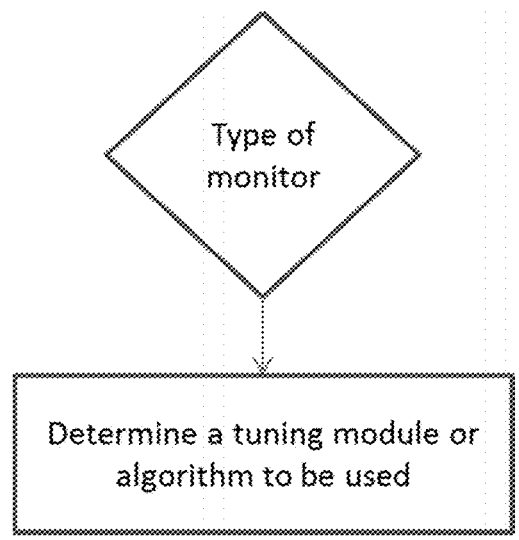
Figure 17B:
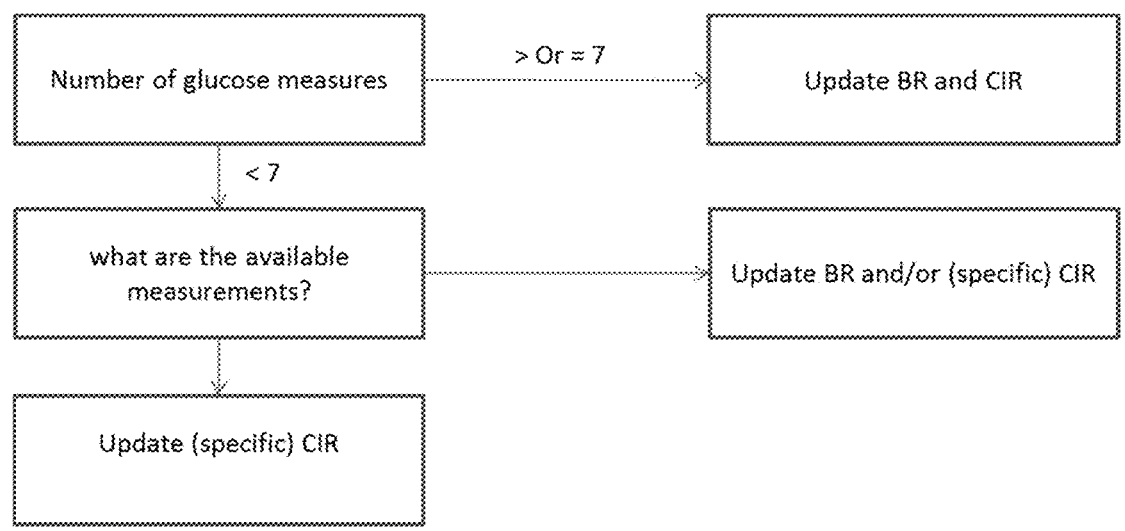

As illustrated by the FIGS. 17a and 17b, the blood glucose measurements may be used to determine:

which part of the therapy may be changed as explained below, and/or how to compute the change (which algorithm to be used) (which may depend on the type of glucose monitoring device (CGM or SMBG) or the number of available measurements).

The method may further comprise the step of:

determining the type of glucose monitor used for the measurements (for example SMBG or CGM or manual measure or automatic measure, . . . ), and/or determining the tuning module (or computer-executable instructions) to be used (for example from a predetermined list) or the algorithm to be used by the tuning module. This step may depend on the type of glucose monitoring device or the number of available measurements.

Thus, the system may allow the patient to change the type of glucose monitoring device over the treatment, for example from a CGM to a BGM and/or vice versa.

To determine the type of glucose monitor used for the measurements, the user or the patient may select the type of glucose monitor used or the system may automatically determine the type of glucose monitor used. For example, the computer-executable instructions may determine the type of glucose monitor depending on the number of available measurements or depending on an information sent by the type of glucose monitor used to the system.

Figure 16:
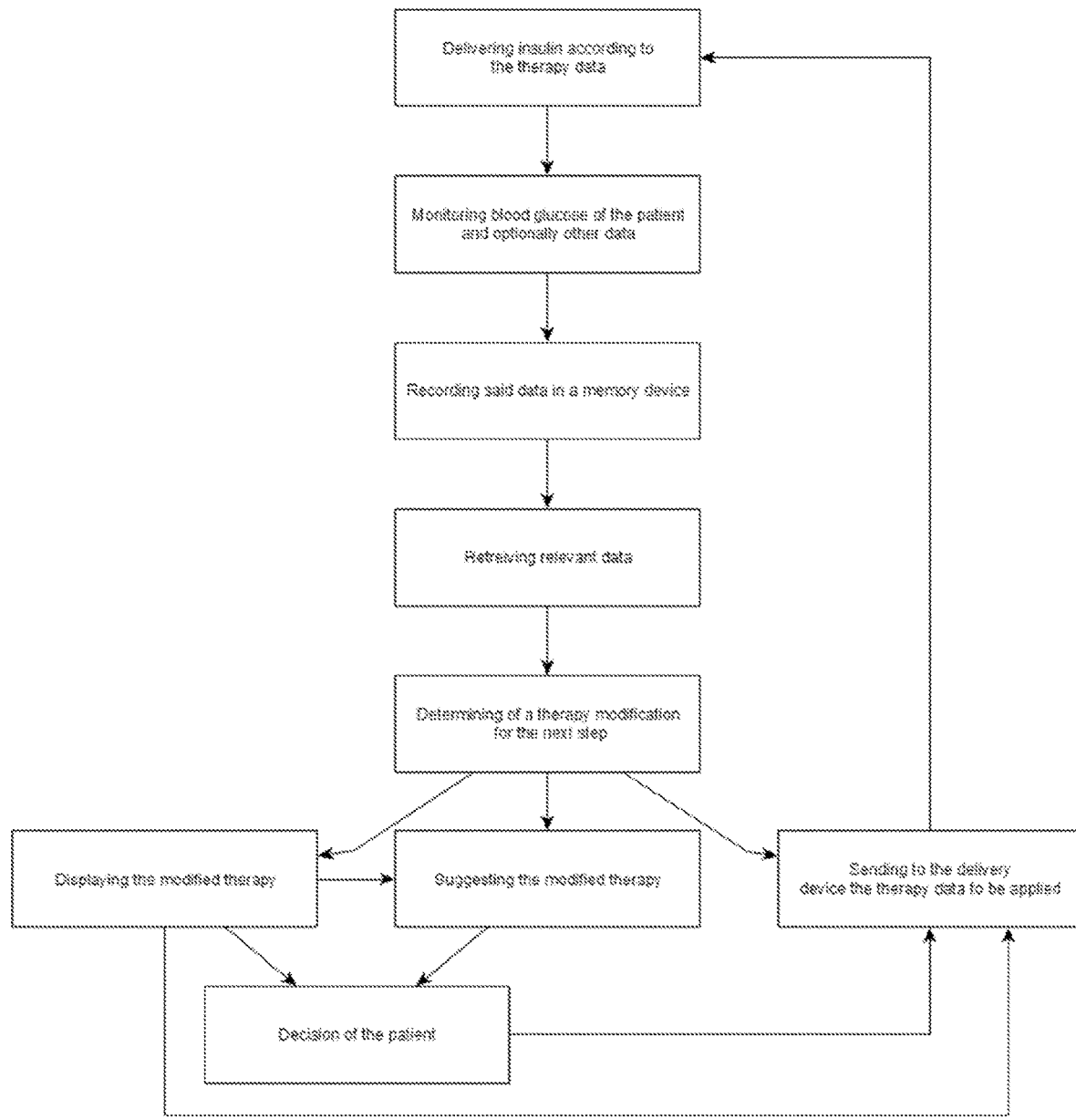

As described by the flowchart of the FIG. 16, the method may further comprise at least one of the following steps of:

displaying at least a part of therapy modification;

suggesting to the patient the therapy modification; and/or delivering insulin amount by taking into account the therapy modification for a subsequent time period.

For example, after the step of determining:

the modified therapy may be displayed on a display device of the system, for example in order to:

suggest the modified therapy to the patient, inform the patient to the modification, the modified therapy may be suggested to the patient, the modified therapy may be sent to the delivery device in order to control the delivery device with the modified therapy, the patient may decide to accept the modified therapy or to keep the last therapy or to change the therapy and to send the selected therapy to the delivery device.

The basal rate may comprise only one or several single basal rates for the time-duration of a time-period.

The new basal rate and/or new CIR could be used for a subsequent time-period. The new basal rate and/or the new CIR may be suggested to the patient and the patient can accept or not this proposal. The patient may launch the method, for example after the last measurement of blood glucose level of the current time period. Thus, an aspect of the invention may act as a coach which suggests a therapy management, but the patient can choose between the suggested parameter of other.

In case of closed loop, the new basal rate and/or the new CIR will be automatically used for the subsequent time-period.

Preferentially, the amended CIR is used for computing at least one bolus for at least one meal of the subsequent time-period.

Preferentially, the method is repeated for each new time-period and the subsequent time-period may start substantially at the end of the first time-period or at the end of the previous time-period.

The method according to an aspect of the invention may further comprise the step of retrieving from the memory device data associated to the carbohydrate of at least one meal eaten by the patient over said first time-period.

Optionally, the processor unit improves the medication delivery parameter (for example the basal rate) (and/or the CIR) at each subsequent time-period (for example day after day). In this case, the method may further comprise the steps of:

optionally, retrieving from the memory device at least two measurements of blood glucose of a patient (performed by a SMBG and/or a CGM) over at least one past time-period; or retrieving from the memory device the medication delivery parameters executed over at least one past time-period, including at least one of a basal rate and a bolus; or retrieving from the memory device data associated to the CIR of the patient over said at least one past time-period;

It is to be understood that the past time-period is older than the first time-period. In this case, the process unit may take into account all or a part of the retrieved from the memory device data of one or more past time-periods.

The method according to an aspect of the invention may further comprise the step of determining the effective amount of drug delivery during at least a part of the first time-period and the processor unit may take into account said effective amount of drug delivery for determining the therapy for a subsequent time-period.

The method may comprise a preliminary phase called initialization phase, during which a CGM may be used.

Example of Product According to an Aspect of the Invention

Figure 6:
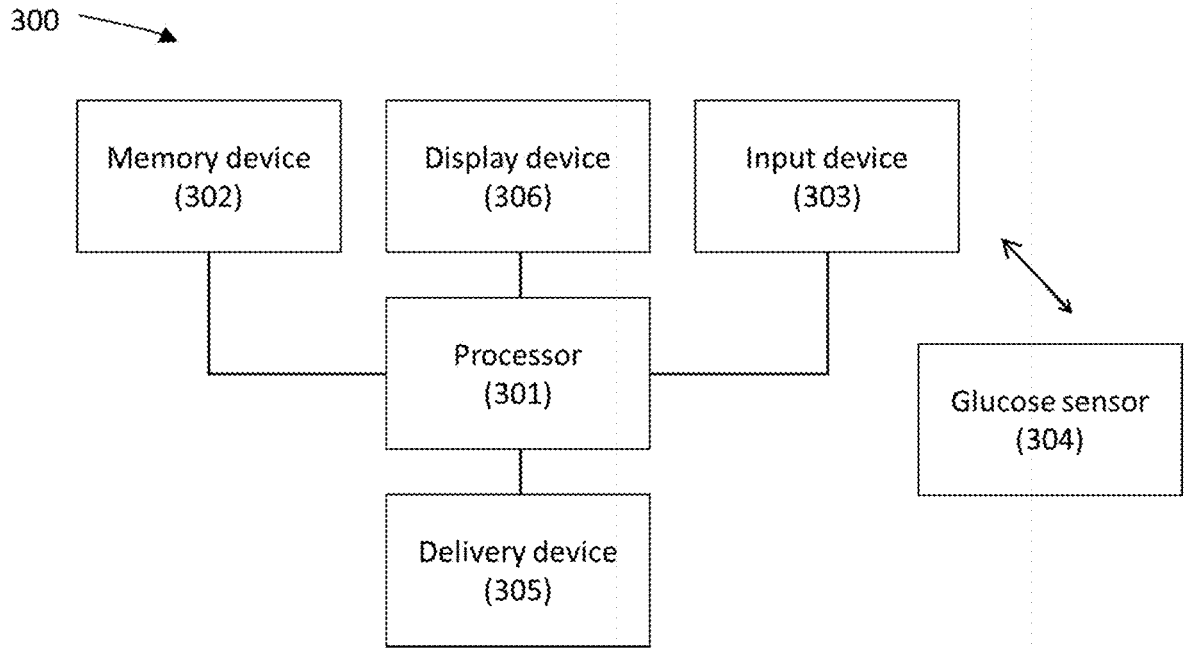
FIG. 6 shows an example of the system according to an aspect of the invention.

As disclosed by the FIG. 6, an aspect of the invention further discloses a system (300) for determining insulin needs of a diabetic patient. The system may comprise:

an input device (also called acquisition device) (303) configured for receiving glucose data relating to a glucose level of the patient;

a delivery device (305) configured for delivering insulin to the patient according to a medication delivery parameter including at least one of a basal rate and a bolus;

a memory device (302) configured to store
at least one glucose data and
at least one of the medication delivery parameter and a CIR relating to the Carbohydrate to Insulin Ratio information of the patient;

a processor (301) configured to execute computer-executable instructions adapted to:
retrieve from the memory device at least two glucose data over a first-time period;
retrieve from the memory device at least one of:
the medication delivery parameter executed by the delivery device over the first time-period; and
the CIR; and
retermine based on at least a part of the retrieved data a therapy modification comprising a modification of at least one of:
the basal rate; and
the CIR The therapy modification is preferentially intended to be used for a subsequent time period by the delivery device (305); and the glucose data are preferentially provided by a Self-Monitoring Blood Glucose.

The computer-executable instructions may be further adapted to:

display at least a part of therapy modification (via for example a display device (306);

suggest to the patient the therapy modification; and/or control the delivery device to deliver an insulin amount by taking into account the therapy modification for a subsequent time period.

The input device may be:

a blood glucose meter having a Glucose sensor (304) such as a BGM or a CGM; or a keyboard (via hard button or touch screen of a remote controller) used to enter manually the data of the blood glucose of the patient measured by an BGM.

The system may comprise a user interface comprising a visual display and the input device configured to receive and communicate user input data and instructions.

The processor may be further programmed to:

predict or compute the hypoglycemia and/or hyperglycemia event so as to alert the patient which may be caused by the current delivery parameter; and/or Predict or compute the hypoglycemia and/or hyperglycemia event which may be caused by the delivery parameter intended to be used for a subsequent time period and may alert the patient.

The system may be used as or may comprise an education module (which may display message on the display device depending on the result provided by the computer-executable instructions) so as to:

educate and/or motivate the patient to modify her/his behaviors, or provide her/him with a better understanding of her illness as well as treatment options, or prompt him/her to be compliant with the treatment.

The computer-executable instructions may take into account less than ten or eight or five measurements of blood glucose of a patient per time period. The time duration of time periods may be predetermined or variable and comprises between 1 hour and 36 hours.

The processor may be configured for determining the effective amount of drug delivered during at least a part of the first time-period.

The processor may be configured for retrieving data associated to the carbohydrate of at least one meal eaten by the patient over said time-period. Furthermore, the processor may be configured to improve the determination process by taking into account at least a part of the retrieved data of several time-periods.

The system may further comprise an activation device configured for launching the computer-executable instructions of the processor. The activation device may be activated by the patient for example after the last measurement of the glucose level of the patient, of the time-period.

Figure 7:
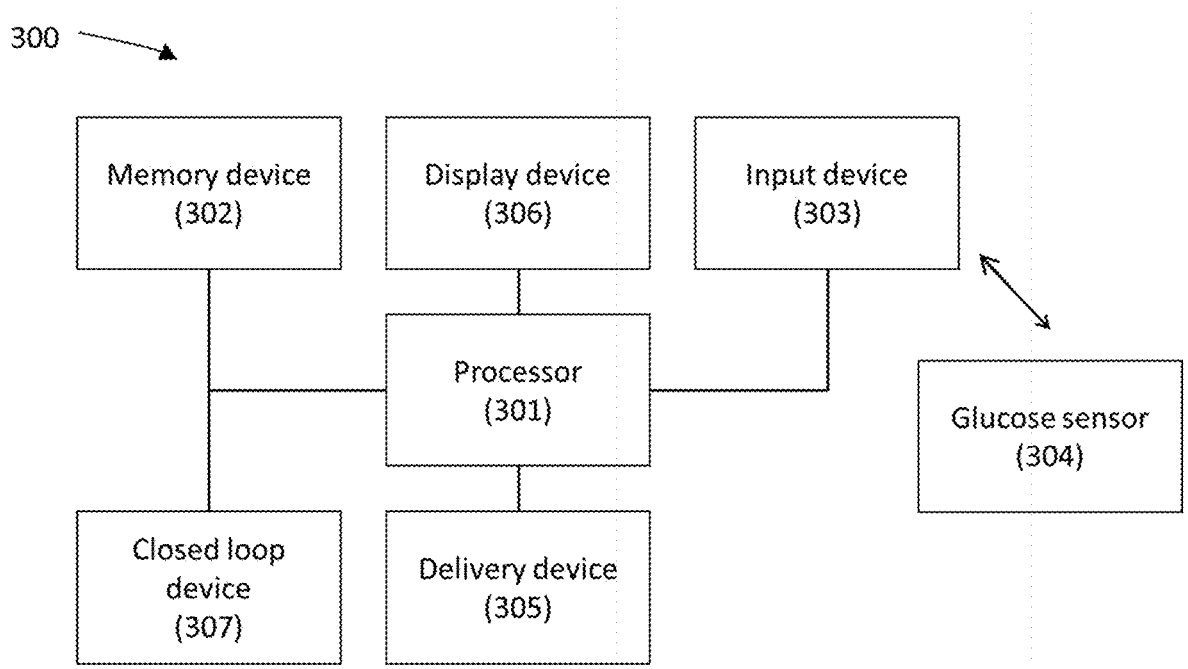
FIG. 7 shows an example of the system according to an aspect of the invention using a closed loop.
Figure 8:
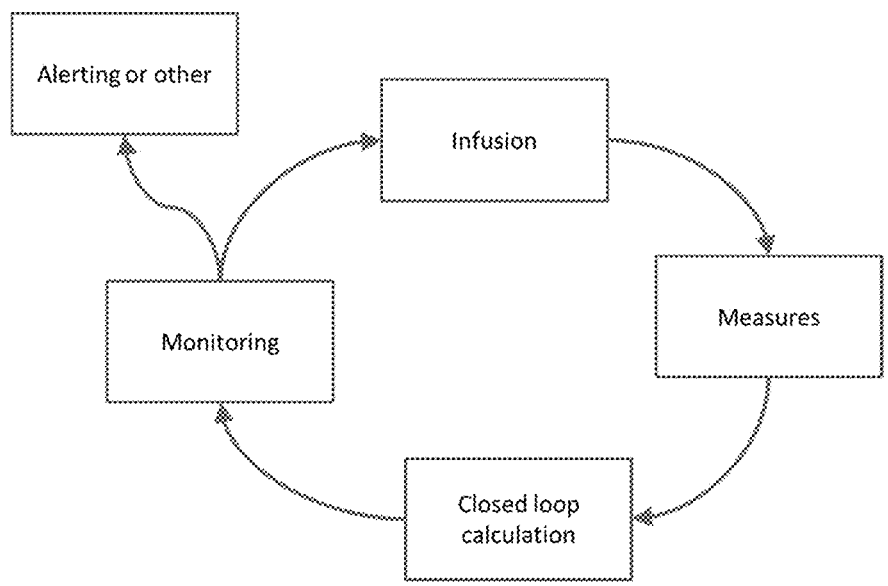
FIG. 8 illustrates an example of monitoring process.

Example of Closed Loop Monitoring Device According to an Aspect of the Invention An aspect of the invention further discloses a system and a method adapted for monitoring a closed loop device, as disclosed by the FIG. 7, the system (300) may comprise:

an acquisition device (303) configured to acquire a plurality of glucose data of the patient for example via a glucose sensor (304);

a closed loop device (307) configured to determine a medication delivery parameter including at least one of a basal rate and a bolus;

a memory device (302) configured to store a plurality of data relating for example to the medication delivery parameter and/or to glucose data;
a delivery device (305) configured to deliver a drug to a patient according to the medication delivery parameter; and
a processor (301) programmed to:
  receive blood glucose data of the patient measured over a predefined time-period;
  receive the medication delivery parameter applied by the delivery device over said predefined time-period;
  determine or calculate a set of acceptable data comprising for example at least one of a basal rate and/or a CIR which may be used for a subsequent time-period, by taking into account the received data;
the processor may be further programmed to:
  receive the medication delivery parameter (and/or CIR) computed by the closed loop device (or intended to be used) for the subsequent time-period; and
  compare the set of acceptable data to the medication delivery parameter (and/or CIR) computed by the closed loop device (or intended to be used) for the subsequent time-period.
The processor may be further programmed to:
  predict or compute the hypoglycemia and/or hyperglycemia event so as to alert the patient which may be caused by the current delivery parameter; and/or
  predict or compute the hypoglycemia and/or hyperglycemia event which may be caused by the delivery parameter calculated by the closed loop device (for the current time-period or a subsequent time-period).
If the difference reaches a predetermined threshold, the processor is programmed to:
  alert the patient or other user, and/or
  suggest another medication delivery parameter in compliance with said acceptable range, and/or
  stop the closed loop device.
An example of the process applied by such device is disclosed by the FIG. 8.
The closed loop system may use glucose data measured by a CGM and the monitoring process may use glucose data measured by a SMBG or a CGM.

Example of Delivery Device

Figure 1B:
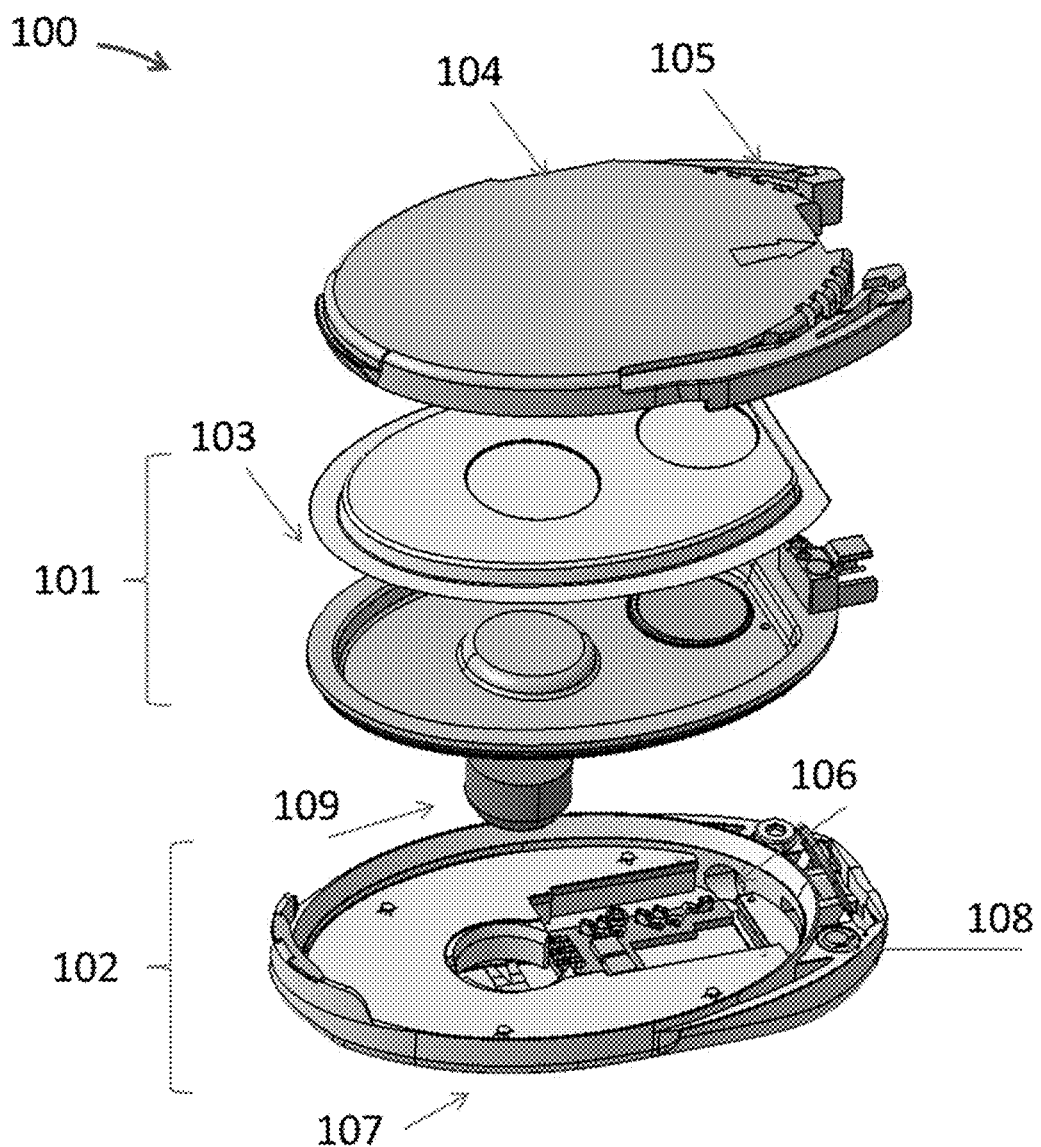

The FIG. 1b shows an example of a delivery device according to an aspect of the invention. The delivery device (100) may comprise two distinct parts. A first part, called disposable part (101), may be discarded after predetermined time duration. The disposable part may be not re-usable after use (single use). A second part, called non-disposable part (102), may be re-usable with different (i.e. successive) disposable parts. The disposable part (101) may be removably attached to the non-disposable part (102) and both form the pumping device. Both have to be attached, preferentially in a tight manner, so that the delivery device (100) works.

The disposable part may comprise a reservoir (103) storing the solution. Said reservoir is arranged into a first cavity closed by a housing (104) which may comprise vent (105) for pressure equilibration (of the cavity with the exterior of the housing). The reservoir comprises an outlet which is in fluid connection with the inlet of the pumping unit.

The non-disposable part (102) may comprise some electronic elements (106) (for example a processor and/or a memory) which are arranged into a second cavity closed by a housing (107) which may comprise a vent (108) for ventilation of the second cavity with a hydrophobic membrane. A battery (109) is used by the delivery device and may need air to operate (for example Zinc-air battery). Preferentially, the housing of the disposable part and the housing of the non-disposable part form at least a part of the housing (112) of the delivery device (100). The non-disposable part may comprise one or more button arranged on the housing, said button is connected to the processor and may control the delivery.

The pumping unit (not shown) or the battery (109) may be arranged into the second cavity. The pumping unit or the battery (109) may be secured against the disposable part.

It is to be understood that other embodiments are contemplated and may be made without departing from the scope or spirit of the present disclosure. Thus the delivery device described above is an example other delivery device may be used with an aspect of the invention such as a fully disposable delivery device or a delivery device without electronics, . . . .

Example of Pumping Unit

The pumping unit may be a "push-pull" device which comprises a pumping chamber (11) designed in such a way to pull the fluid from the reservoir (103) (to the pumping chamber (11)) and push it (from the pumping chamber (11)) to the patient. The great advantage of this type of pumping unit is the delivery accuracy. Indeed, thanks to its pumping chamber, at each stroke, the delivery volume is known.

The pumping unit may comprise:
  a pump actuator (25) adapted to change the volume of the pumping chamber. Said pump actuator may be coupled to the processor in such a way that the processor controls the pump actuator and/or monitors the position of said pump actuator (via for example a sensor). The processor may also deduct the position of the actuator depending on the actuation data.
  An inlet with an optional inlet valve (2) and an outlet with an optional outlet valve (5). Said valves may be check valves. The filling of the pumping chamber is associated with negative relative pressure in the pumping chamber that opens the inlet valve and maintains closed the outlet valve (Pull of pumping membrane), while the infusion corresponds to positive relative pressure in the pumping chamber that opens the outlet valve and maintains closed the inlet valve (Push of the pumping membrane). The inlet of the pumping unit is preferably in fluid connection with an outlet of the reservoir (103) and a filter may be arranged between the reservoir and the pumping unit.
  A pumping membrane (3) (which may be at least partially flexible) adapted to move between at least two positions, preferentially against mechanical stops. Every time the membrane is pulled to fill the pumping chamber, the membrane will come in contact with a mechanical structure that will stop its course (for example against the anti-bonding layers (15)). Every time the said membrane is pushed to empty the pumping chamber, it will come in contact with a mechanical stop that will again stop its course (for example against the anti-bonding layers (14)). Thanks to these mechanical stops, if for example their distance is known and constant, the pumped volume is known with a high accuracy. The system may be adapted to hold a given pumping membrane position, for example against a mechanical stop during a predetermined period of time.

In one embodiment, the delivery system comprises a pumping unit as shown in the FIG. 1a, which may be a reciprocating displacement MEMS. Said figure illustrates a cross section of a micro pump with the stack of a glass layer as base plate (8), a silicon layer as second plate (9), secured to the base plate (8), and a second glass layer (10) as a top plate, secured to the silicon plate 9, thereby defining a pumping chamber (11) having a volume. An actuator (25) linked to the mesa (6) allows the controlled displacement of the pumping membrane (3). A channel (7) is also present in order to connect the outlet control member, the outlet valve (5) to the outer detector not represented here and finally to the outlet port (18) placed on the opposite side of the pump.

The FIG. 1a further illustrates an optional cover (12) onto the channel (7), an outer detector (13), a fluidic channel (17) located downstream of the outlet valve and the outlet port (18). The pressure inside the pumping chamber varies during a pumping cycle depending on numerous factors, such as the actuation rate, the pressure at the inlet and the outlet, the potential presence of a bubble inside of the chamber, the valve characteristics and their leak rates.

The MEMS technology is suitable for the implementation of an integrated piezo-resistive gauge pressure sensor (4, 13) in the silicon chip. Thanks to the very large piezo-resistance factor of silicon, these sensors exhibit outstanding sensitivities, low dead volume, no hysteresis, small offset when using the so called Wheatstone bridge configuration and good linearity, the single drawback being a temperature dependence of the signal.

A first membrane (4) with strain gauges in Wheatstone bridge configuration may be placed in the pumping chamber to monitor the good functioning of the pump while another sensor (13) may be placed downstream of the outlet valve for occlusion detection purpose.

The characteristics of these gauge pressure sensors, the implantation profiles as well as the location of the resistors have been optimized to get a detector with an offset of about a few hundredths of uV/V/bar and typical sensitivity from 10 to 50 of mV/V/bar in the range −1 to +1.5 bar, with a minimum resolution of 1 mbar or less. After taking into account the different errors related to mask alignments, implantation, membrane etching, position of the resistors with respect to the membrane and the crystallographic axis, the detector signal variability has been estimated at +/−7.6% at 20° C.

The pressure sensor may be also used to monitor the amount which has been effectively delivered (for example during the time period) to the patient, for example depending on the pressure data the processor may estimate this effective amount. The processor unit may compare the effective amount and the therapy data (for example the basal rate) and may take into account for determining a new optimal therapy.

It is to be understood that other embodiments are contemplated and may be made without departing from the scope or spirit of the present disclosure. Thus, the pumping unit described above is an example other pumping unit may be used with an aspect of the invention such as syringe pump or other.

Other Optional Features of Delivery System

Figure 1C:
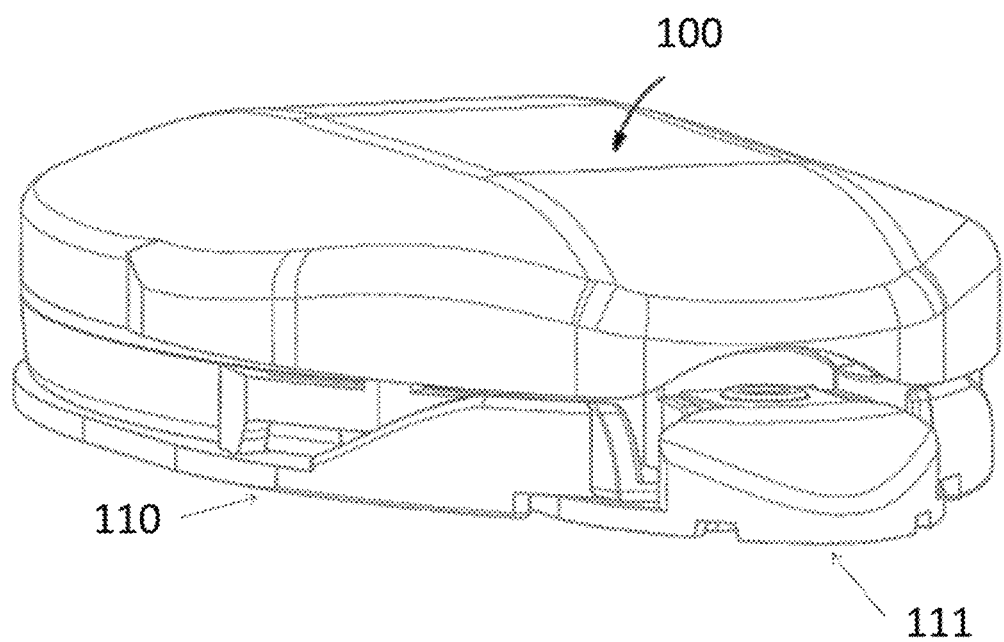

The FIG. 1c shows the delivery device (100) of the delivery system (also called medical system). The delivery device may be designed in such a manner as to be worn directly on a patient's skin. In this embodiment, the delivery system comprises a patch (110) adapted to be secured (via adhesive) against the skin of the patient. The patch comprises attachment elements so as to removably secure the delivery device to the patch. The system further comprises an infusion set (111) which may be removably coupled to the delivery device (100). The infusion set may be removably coupled to the patch (110) or the infusion set, and the patch may be formed within a single piece. The delivery device may comprise a sensor (hall effect sensor) (not shown) adapted to detect when the delivery device is correctly coupled to the infusion set. Said sensor is preferentially connected to the processor of the delivery device (100).

When the delivery device and the infusion set are correctly coupled, a fluidic pathway is created. Said fluidic pathway extends from the reservoir to the infusion site.

Figure 1D:
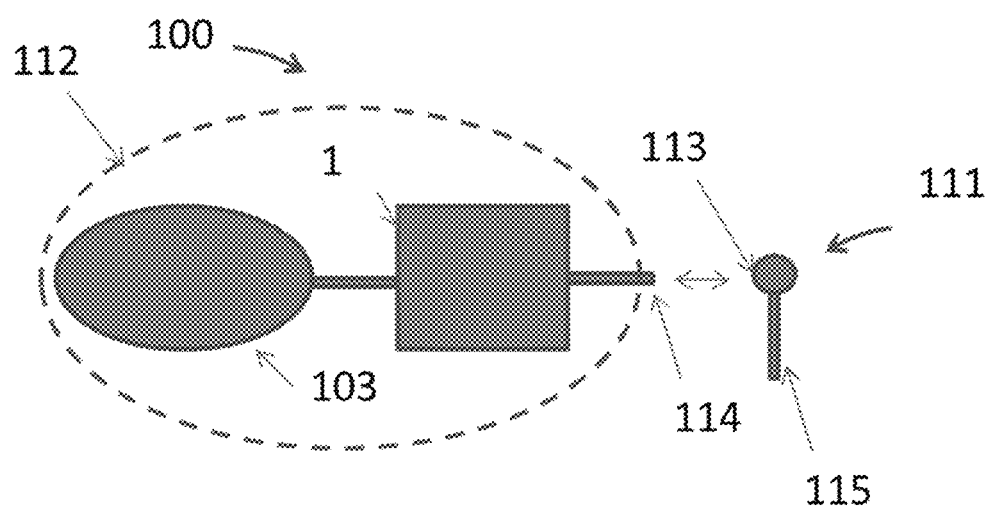

The FIG. 1d shows a schematic of the delivery device (100) which is disconnected from the infusion set (111). The delivery device comprises a housing (112) in which a reservoir and a pumping unit are arranged. The delivery device (100) further comprises an outlet port (114) adapted to be connected (in fluid communication) to an inlet port (113) of the infusion set (111) when the delivery device and the infusion set are coupled. Said infusion set further comprises a cannula (115), a needle or a micro needle.

Figure 1E:
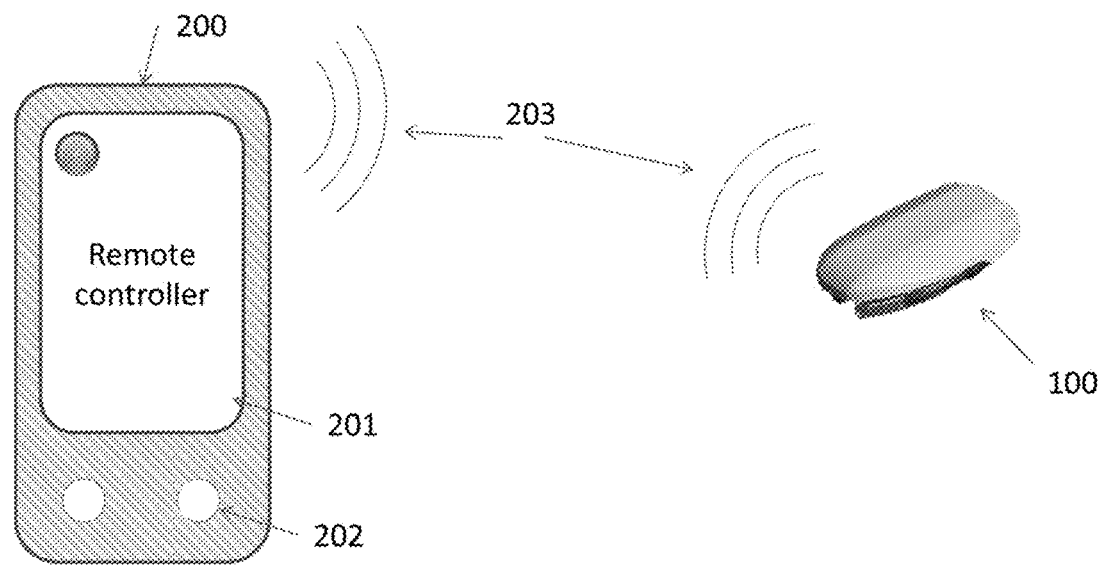
Figure 2:
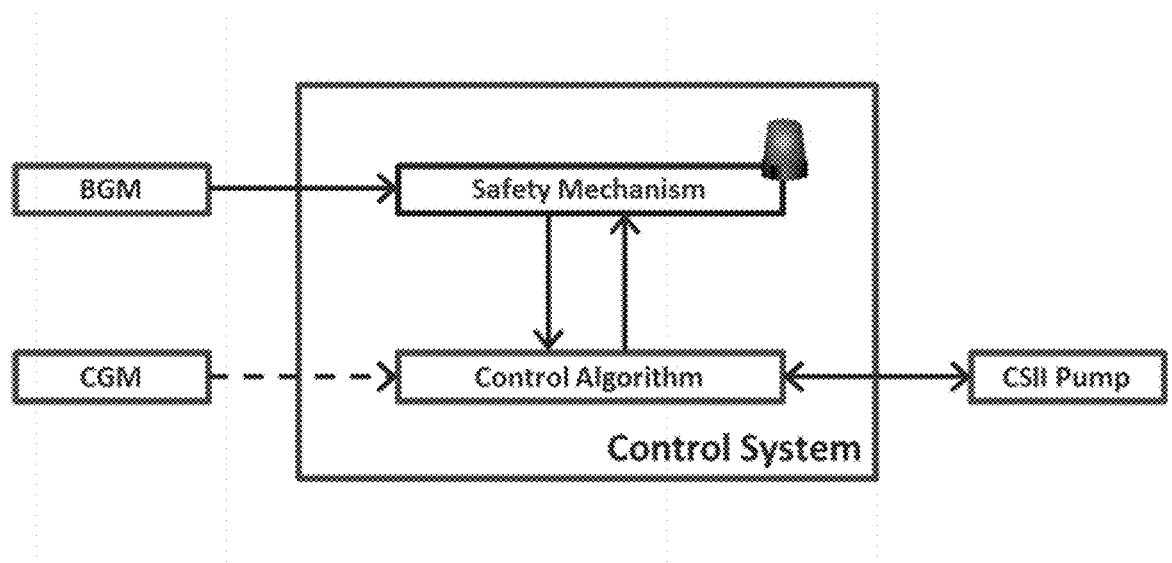
FIG. 2 illustrates a control system with the control algorithm and the safety mechanism.
Figure 3:
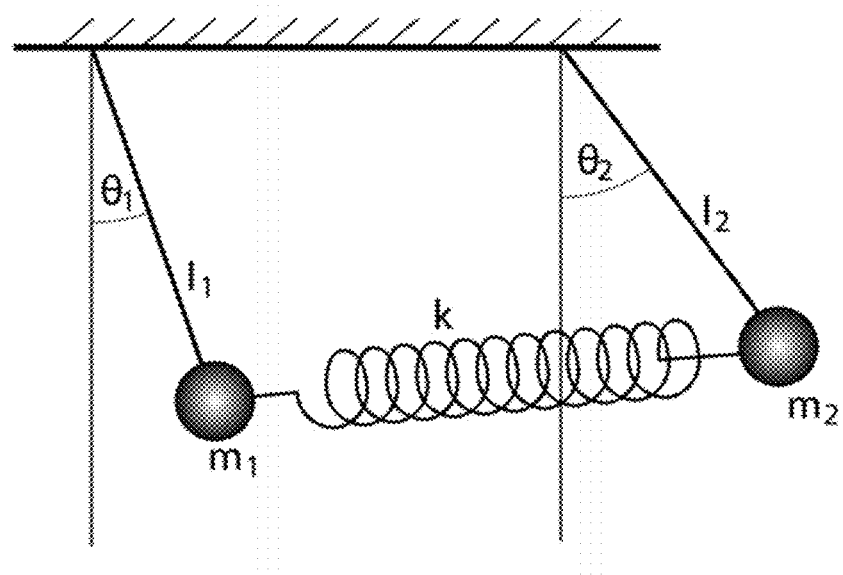
FIG. 3 illustrates coupled oscillators.

In one example as shown in the FIG. 1e, the delivery system further comprises a remote controller (200). Said remote controller is adapted to command and program the delivery device (100) and it is used as an interface between a user and the delivery device (100). Preferentially, the remote device and the delivery device are two distinct devices. Thus, the delivery device may comprise its own electronic device including processor and memory and the remote controller may comprise its own electronic device including processor and memory.

The remote controller (200) comprises a screen (201) (for example a touch screen) and, optionally, at least one button (202). The remote controller (200) and the delivery device (100) comprise telecommunication devices (203) which allow exchanging data between the delivery device and the remote controller via a wireless communication. At least one telecommunication device may be arranged in the housing of the remote controller or in the housing of the pumping device. Said telecommunication device exchanges data from the delivery device to the remote controller and from the remote controller to the delivery device via wireless communication (for example Radio Frequency, Bluetooth, BLTE, WIFI, Zigbee, . . . ).

The system may comprise an analyte-measurement device that is used to evaluate a concentration of analyte in bodily fluid. The analyte-measurement device may be arranged in the remote controller (for example inside the housing of the remote controller) or in a distinct device. The analyte-measurement device may be a BGM used to measure the glucose level present in a body fluid of the patient. The memory of the remote controller may be configured to store one or more BG measurements of one or more period of time. The remote controller may comprise an input device configured to enter the data of the BG measurements.

The system may further comprise a memory device configured to store glucose level data, therapy management, software, therapy history, patient data, . . . . For example, this memory device may be arranged into the remote controller and connected to the processor of the remote controller.

The system may further comprise a wearable sensor device secured against the patient skin wherein said remote sensor device is adapted to monitor for example the blood glucose level of the patient on a regular basis.

Algorithm Used with the Method According to an Aspect of the Invention

The product according to an aspect of the invention may include (or the method according to an aspect of the invention may use) a new nonlinear control approach with main characteristic the ability of learning and online adaptation in order to optimize its performance over time and overcome the intrinsic system delays and uncertainties due to subject variability and to the multiplicity of disturbances. Furthermore, a model free approach may be adopted for the design of the controller device in order to avoid the modeling associated errors. Safety mechanisms based on artificial intelligence approaches may ensure that the controller prevents insulin overdose and hypoglycemic events.

A novel control algorithm for the glucose regulation in patients with T1D may be introduced based on reinforcement learning and optimal control; the Actor Critic (AC) learning algorithm. Main principle of the AC is the performance optimization over time based on a continuous interaction with the system under control and its environment and the respective adaptation of the control policy. The AC algorithm has found great acceptance and successful implementation in the control of non-linear, high dimensional, stochastic systems, characteristics that imply the need for an adaptive learning and robust approach.

For further details with regard to an Actor Critic (AC) learning algorithm is describes in the PCT application WO 2018/011766 A1, the content of this PCT application is incorporated by reference in the present account.

AC consists of two complementary parts: the Critic and the Actor. At each time step of the algorithm, the Critic provides an approximation of the cost-to-go, i.e. the future cost of the system based on the Temporal Differences (TD) method. The Actor implements a parameterized control policy, which is optimized based on the Critic's estimations by appropriate update of the parameters.

AC may be implemented in a model-free approach, in the sense that no mathematical model of the system may be used either for design or for prediction purposes. Both Actor and Critic base their function on information regarding current glucose measurement, glucose past, glucose trends, IOB, as well as timing and amount of the upcoming meal.

In order to ensure the safety of the closed-loop, safety mechanisms may be designed based on the combined use of data-driven models and constrains related to IOB in order to reduce or suspend the suggested by the AC controller insulin infusion rate. Maximum allowed IOB values will be defined, which when exceeded, will lead to pump shut-off in order to avoid possible hypoglycemic events. Furthermore, an alarming mechanism will be designed for the detection of upcoming hypoglycemic events. Alarming an upcoming hypoglycemia is crucial for the immediate suspension of insulin infusion and the information of the patient in order to take actions and increase his/her glucose levels.

Other control algorithms for glucose regulation may be used with the method according to an aspect of the invention such as without limitation:

Proportional-Integral-Derivative (PID) controller,

Model Predictive Controller (MPC),

Run-to-Run algorithm,

Optimal Control (OC),

MD-Logic (MDL), or

Bi-hormonal glucose regulation, . . . .

How the SMBG Data May be Taken into Account to Modify the Therapy
Basal Rate and/or CIR(s)

Figure 4:
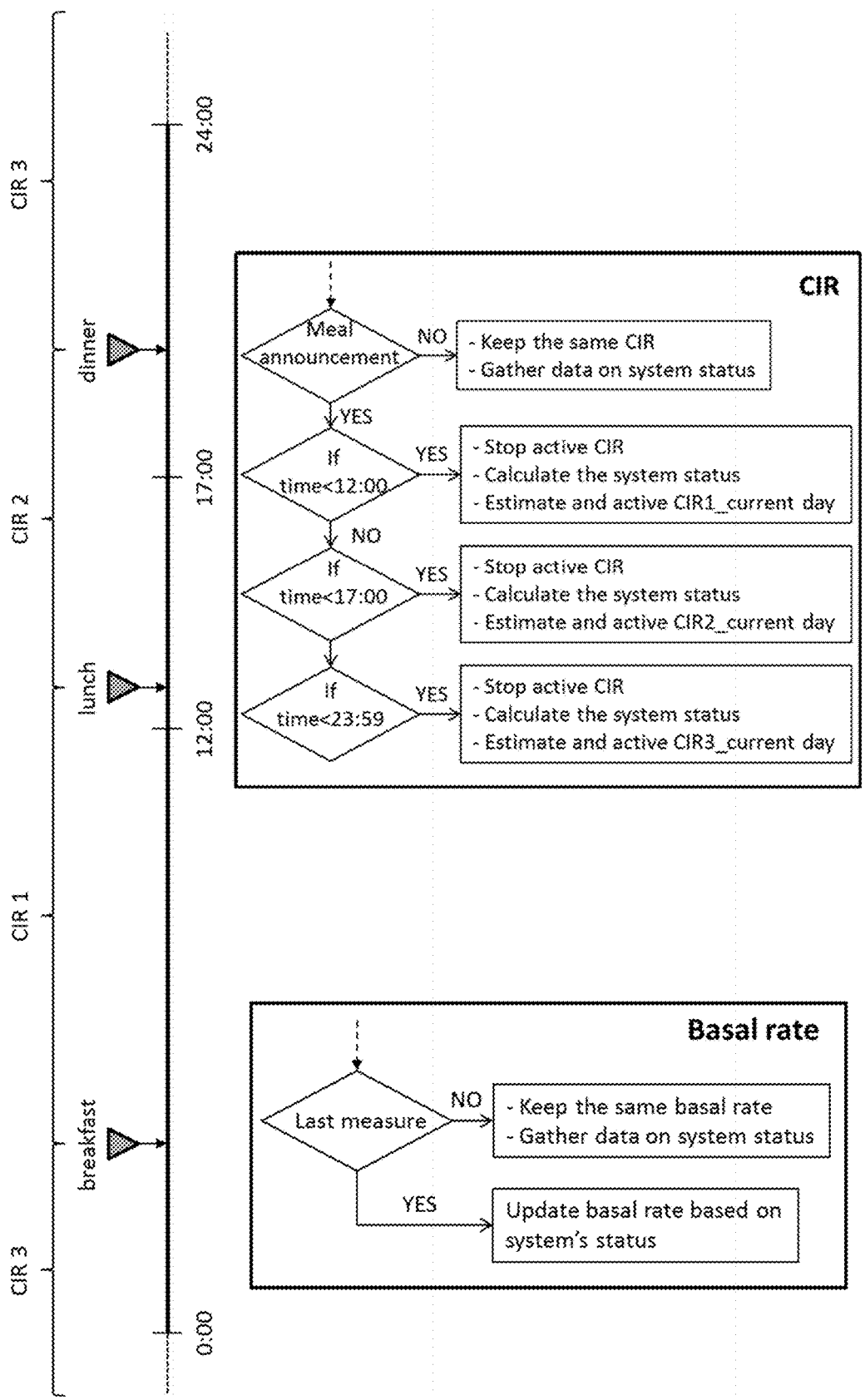
FIG. 4 illustrates an example of update of basal rate and CIR in one day.

According to an aspect of the invention, a novel algorithmic approach for the daily adaptation of the insulin delivery settings (basal rate (BR) and/or CIR) without the involvement of clinicians, engineers or patients is introduced. To address the intra-day variation cycles, as well as inter-day insulin sensitivity (SI) variation, three different CIRs for breakfast, lunch and dinner may be calculated. Since variability of Basal Rate profiles is associated with an increased frequency of acute complications in adults with T1 D, the use of a flat Basal Rate profile (if no intensive physical exercise is involved) updated on daily basis may be considered. The flowchart of the FIG. 4 illustrates the daily adaptation process of BR (up) and CIRs (down).
Effects of SMBG According to the NICE guideline [NICE guideline [NG17] (2015). Type 1 diabetes in adults: diagnosis and management] a minimum of four (4) times daily SMBG should be considered. Preferentially, the novel algorithm holds this requirement. The SMBGs could be pre-meal measurements (20 minutes before meal), post-meal measurements (2 hours after meal) or a bedtime measurement (at 23:00). The algorithm may be adapted to able to tolerate errors in the announcement of the BGM in the order of +/−15 minutes. It has to be noted, that the SMBG can take place at any time before and after the meal (e.g. 40 min before meal with +/−15 min error in time of SMBG announcement).

Preferentially, the three pre-meal measurements may be mandatory. The additional measurements can be either a bedtime measurement or post-meal measurements.
Basal Rate The basal rate may be updated based on the fasting SMBGs, either three pre-meal measurements, or three pre-meal measurements plus bedtime measurement.
CIR The CIRs for each of the main meals (breakfast, lunch or dinner) of the current day may be updated based on the glucose measurement(s) for the corresponding meal of the previous day and/or the latest pre-meal SMBG. If the previous day's post-meal measurement for the corresponding meal is available, it may also be taken into consideration.

EXAMPLES

In case all the four fasting SMBGs are available, these four fasting measurements may be employed for adjusting the BR. CIR may be updated based on the corresponding pre-meal measurement.

In case the four measurements include three pre-meal measurements and one post-breakfast measurement, basal rate may be updated based on the three pre-measurements and the CIR for breakfast may be updated based on pre- and post-breakfast measurements, while the CIRs for lunch and dinner may be updated based on their pre-meal measurements only.

When daily 7 measurements (for example 3 pre-meal measurements, 3 post meal measurements and 1 bedtime measurement) are available, then basal rate may be updated based on the last day's 4 fasting measurements, while each CIR may be updated based on the corresponding pre- and post-meal measurements of the last day.

The FIG. 16 illustrates a flowchart to determine the data to be changed.

Example Algorithm in Glucose Regulation and Primary Results

The delivery system described in this document may use the algorithm based on Actor-Critic (AC) learning. AC belongs to the class of reinforcement learning (RL) algorithm and consists of two complementary adaptive agents: the Critic and the Actor, with the former being responsible for the control policy evaluation and the latter for the control policy optimization.

The system can be modeled as a Markov Decision Process (MDP) with a finite state space X and an action space U. The aim of the agent is to find an optimal policy, in order to minimize the expected cost throughout its path. Transition between states x and y depends on the chosen control action u and follows a transition probability distribution p(y|x,u). A local cost c(x,u) is associated with each state and action. The aim of the AC algorithm is to find an optimal control policy in order to minimize the average expected cost per state over all states. The update period of the control policy in this example was set to 24 hours (one day). Thus, the algorithm offers an adaptive blood glucose control by providing daily updates of the basal rate and CIR (profile).

FIG. 4 illustrates a schematic view and flowchart of an example update of basal rate and CIR profile in one day. In this example, a flat basal rate and a CIR profile with three CIRs per day are employed. The system gathers data during the whole day to evaluate the current basal rate. By the last measure of BG, the system updates basal rate for next day based on the evaluation of the gathered data. When a meal is announced, a corresponding CIR value is activated, which is updated based on the data gathered during the corresponding time-period on the previous day.

Figure 5A:
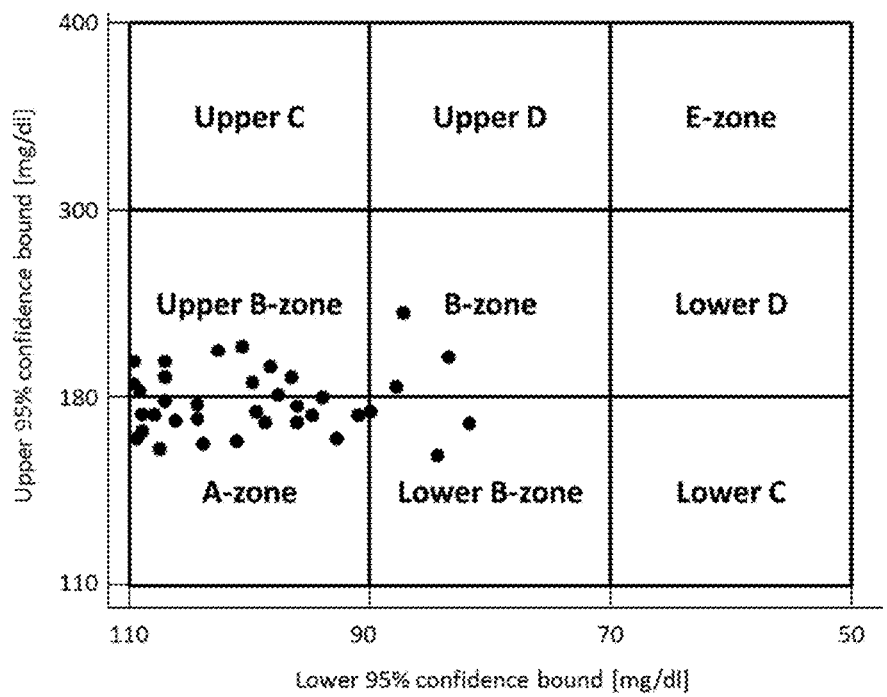
FIG. 5 shows primary in silico evaluation results of a use example in terms of Control Variability Grid Analysis (CVGA).
Figure 5B:
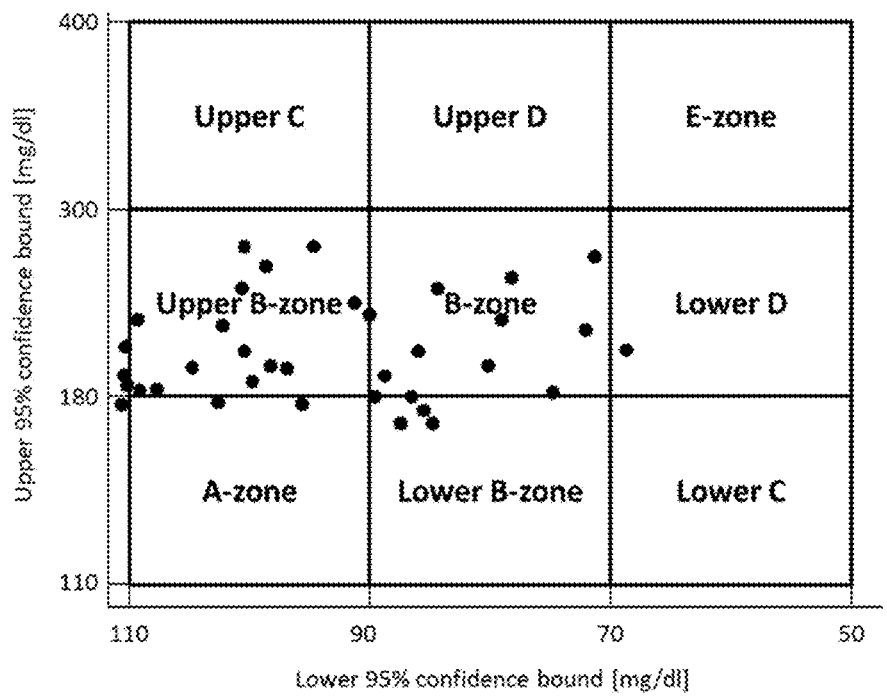
Figure 5C:
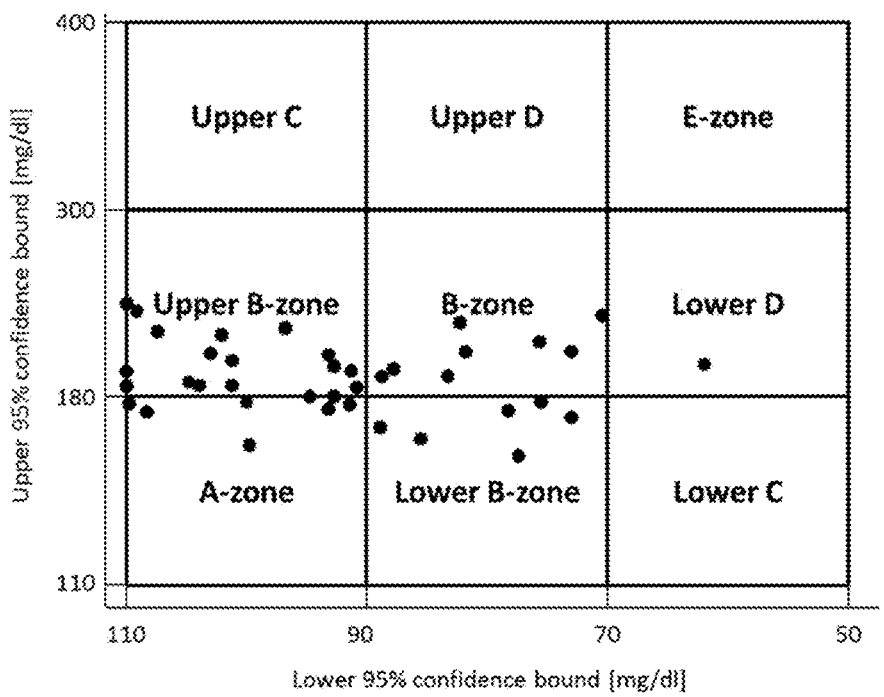

The example AC algorithm was evaluated in silico with the U.S. Food and Drug Administration (FDA) approved UVa Padova T1DM Simulator v3.2. FIG. 5 shows the primary evaluation results in terms of Control Variability Grid Analysis (CVGA), while Table 1 shows the results of the same experiments but in terms of BG levels. The duration of the example experiments were 60 days. By "Open Loop" (OL) the experiments were conducted with the basal rate and CIR given by the simulator during the whole simulation process (60 days). By "Algorithm" an example AC algorithm was employed: in the first 4 days was the aforementioned initialization process and in the next 55 days the AC algorithm daily updated basal rate and CIR profile. The insulin sensitivity variation ("dawn phenomenon") and a random meal uncertainty uniformly distributed between −25% and +25% were introduced. The results were evaluated based on the last 5 days of the experiments.

According to FIG. 5 (Left: Adults, Middle: Adolescents, Right: Children), in this use example, the percentage in A+B Zone for each group was at least 97%. From Table 1 it is clear that the percentage in euglycemia for each age group was increased, while the percentage in hyperglycemia was decreased for all patients. Finally, the percentage in hypoglycemia was decreased for all the adults and adolescents.

Examples of Results Using CGM and SMBG

Figure 9:
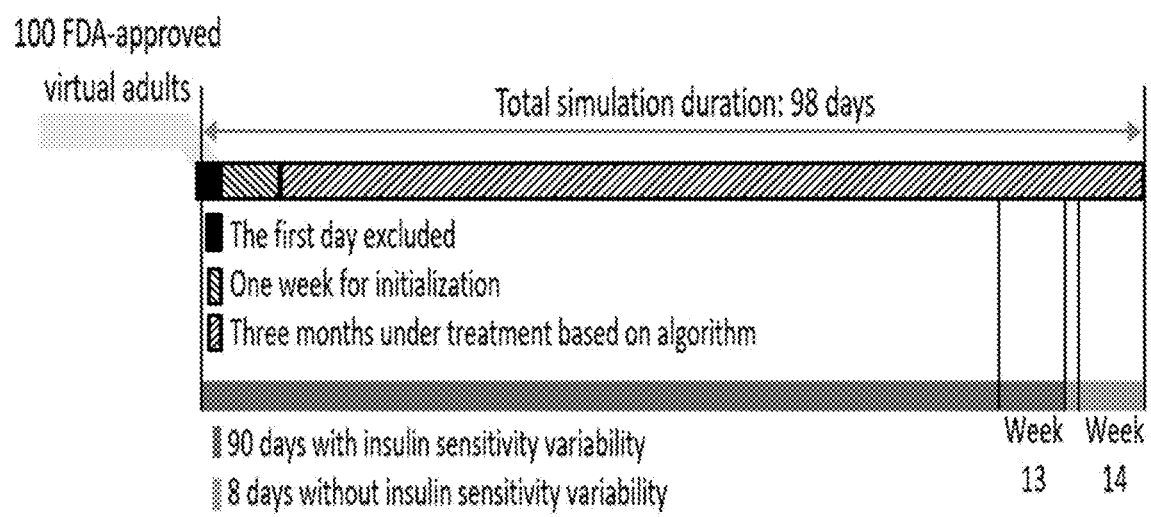
FIG. 9 illustrates an example of in silico evaluation settings.

Both CGM and SMBG versions of the algorithm were in silico evaluated using the 100 FDA-approved adult population under the following configuration (the outline of in silico trail is shown in FIG. 9):

A. Glucose Sensor

CGM version: Dexcom 50

SMBG version: 4 fasting measurements per day (NOTE: With the training version of the simulator, which involves 11 patients, the algorithm was evaluated with 1 to 7 daily BGM measurements. The algorithm with 4 daily SMBG measurements was evaluated with 100 FDA-approved adult population, since according to the NICE guideline [NG17] a minimum of four (4) times daily SMBG measurements should be considered.)

B. Meal Protocol

| Meal type | Breakfast | Lunch | Dinner | Bedtime-snack |
|---|---|---|---|---|
| Meal time | 7:00 h | 12:00 h | 18:30 h | 23:00 h |
| CHO content | 50 g | 60 g | 80 g | 15 g |

Meal time variability: ±15 min

CHO content variability: main meal ±10 g, snacks±5 g

Measurement timing: 20 min before meal

Uncertainty in CHO estimation: ±50%

C. Implemented Hypothesis

Trial duration: 98 days (First day excluded+1 week initialization+3 months under treatment based on algorithm)

Insulin sensitivity (SI) variability: Dawn phenomenon (−50%), ±25% inter-day [1 week initialization+12 weeks under treatment based on algorithm]

Dawn phenomenon scheme: SI change to 0.5 every day from 4:00 AM to 8:00 AM

Evaluation phase: Week 13 (with SI) and Week 14 (without SI)

Sport: No

Bolus for snacks: No

TABLE 1

Results of week 13 (with SI variability)

| Week 13 (with SI variability) | % in target range | % in Hypo | % in Severe Hypo | % in Hyper | % in Severe Hyper | TDI |
|---|---|---|---|---|---|---|
| | | | (mean ± standard deviation) | | | |
| Adults | | | | | | |
| CGM version | 85.9 ± 12.9 | 1.0 ± 1.0 | 0.3 ± 0.8 | 12.8 ± 12.1 | 0.0 ± 0.0 | 42.3 ± 10.2 |
| SMBG version | 84.2 ± 12.8 | 0.5 ± 0.8 | 0.2 ± 0.6 | 15.2 ± 12.4 | 0.0 ± 0.0 | 41.3 ± 9.8 |

TABLE 2

| Week 14 (Without SI variability) | % in target range | % in Hypo | % in Severe Hypo | % in Hyper | % in Severe Hyper | TDI |
|---|---|---|---|---|---|---|
| | | | (mean ± standard deviation) | | | |
| Adults | | | | | | |
| CGM version | 89.8 ± 7.9 | 0.3 ± 0.9 | 0.1 ± 0.5 | 9.8 ± 7.5 | 0 ± 0.1 | 42.4 ± 10.2 |
| SMBG version | 88.5 ± 8.8 | 0.2 ± 0.6 | 0.1 ± 0.4 | 11.2 ± 8.4 | 0.1 ± 0.4 | 41.4 ± 9.9 |

Results of week 14 (without SI variability)

Figure 10:
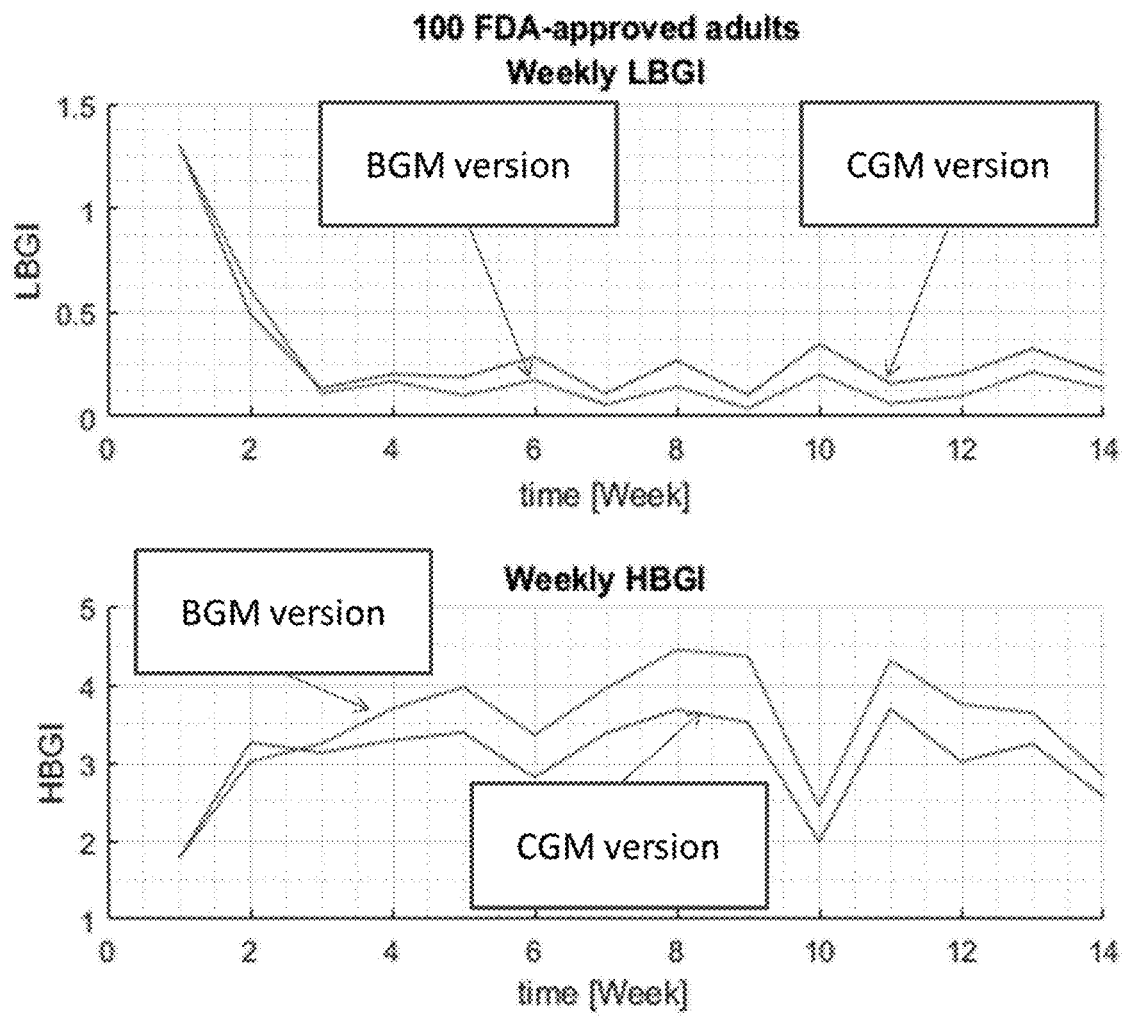
FIG. 10 shows a comparative between CGM and BGM used by the method.

According to Table 1 and Table 2, SMBG and CGM versions of the algorithm achieved comparable performances. The percentage in target zone were very similar, while SMBG version achieved to reduce the hypoglycemic events, while the number of hyperglycemic events was slightly increased. Furthermore, FIG. 10 shows that after the initialization phase, both versions reduced the LBGI from "Low" to "Minimal" without increasing the level of HBGI. Note of the FIG. 10: Weekly low blood glucose index (LBGI) and high blood glucose index (HBGI). LBGI: <=1.1 (Minimal), 1.1-2.5 (Low), 2.5-5.0 (Medium), >5 (High). HBGI: <=5 (Minimal), 5-10 (Low), 10-15 (Medium), >15 (High).

The invention claimed is:

1. A system for diabetes management of a patient, the system configured to provide a daily therapy to the patient, the system comprising:
    an input device configured to receive glucose data relating to a glucose level of the patient;
    a delivery device configured to deliver insulin to the patient according to a medication delivery parameter, the medication delivery parameter including a basal rate or a bolus;
    a memory device configured to store
        glucose data, and
        the medication delivery parameter or a Carbohydrate to Insulin Ratio (CIR) information of the patient; and
    a tuning module including a data processor, the data processor configured to
        retrieve, from the memory device, glucose data comprising at least two glucose measurements performed over a day by a self-monitoring blood glucose device;
        retrieve, from the memory device, the medication delivery parameter executed by the delivery device over the day or the CIR, and
        determine, based on the retrieved data, a therapy modification including a modification of the basal rate or the CIR,
    wherein the therapy modification is intended to the patient for a subsequent time period.

2. The system of claim 1 further comprising a user interface including a visual display to display at least a part of the therapy modification.

3. The system of claim 1, wherein the tuning module is configured to suggest the therapy modification to the patient, and
    the delivery device is configured to apply the therapy modification after the patient accepts the therapy modification.

4. The system of claim 1, wherein the tuning module is configured to learn a usual custom of the patient and to take into account a usage of the patient for determining the therapy modification.

5. The system of claim 4, wherein the usual custom of the patient includes a data mistake inputted by the patient, an over-evaluation, or under-evaluation of carbohydrates includes in a meal of the patient.

6. The system of claim 1, wherein the tuning module is configured to retrieve data associated to a carbohydrate of a meal eaten by the patient over the day.

7. The system of claim 1, wherein the tuning module is configured to take into account less than ten measurements of blood glucose of a patient per day.

8. The system of claim 1, wherein the tuning module is configured to improve the determining of the therapy modification by taking into account at least a part of the retrieved data of several days.

9. The system of claim 1, wherein a time duration of subsequent time period is predetermined or variable and is between 1 hour and 36 hours.

10. The system of claim 1, wherein the tuning module is configured to determine an effective amount of drug delivered during at least a part of the day.

11. The system of claim 1 further comprising:
    an activation device configured to launch the retrieving and the determining of the tuning module.

12. The system of claim 11, wherein the activation device is activated by the patient.

13. The system of claim 11, wherein the activation device is activated by the patient after a last measurement of the glucose level of the patient of the day.

14. The system of claim 1, wherein the tuning module uses an Actor Critic learning algorithm.

15. The system of claim 1 further comprising:
    a continuous glucose monitoring device.

16. The system of claim 1, wherein the tuning module is configured to update the basal rate when daily glucose data includes at least four glucose measurements.

17. The system of claim 1, wherein the tuning module is configured to update the CIR when daily glucose data includes a pre-meal measurement.

18. The system of claim 1, wherein the tuning module is configured to update the basal rate and the CIR when daily glucose data includes at least seven glucose measurements.

19. A non-transitory computer readable medium having computer instructions recorded thereon, the computer instructions configured to perform a method for determining a medication delivery parameter or Carbohydrate to Insulin Ratio (CIR) information independently of the type of glucose monitoring device used when the computer instructions are executed on a data processor of a diabetes management system, the method comprising the steps of:
    obtaining daily glucose data including at least two measurements of glucose level of the patient, the at least two measurements performed over a day;
    obtaining a medication delivery parameter executed over the day, the medication delivery parameter including a basal rate or a bolus, or obtaining a CIR of the patient, the CIR used for calculating a bolus during the day; and determining a medication delivery parameter or a CIR to be used for a subsequent time period, by taking into account the obtained data of the step of obtaining.

20. A method for performing diabetes management on a closed loop device, the method comprising steps of:

obtaining daily glucose data including at least two measurements of glucose level of a patient performed over a day;

obtaining a medication delivery parameter executed over the day, the medication delivery parameter including a basal rate or a bolus, or obtaining a CIR of the patient used for calculating a bolus during the day;

determining a set of acceptable data including a basal rate or a CIR to be used for a subsequent time period, by taking into account the obtained data;

comparing the set of acceptable data to data computed by the closed loop device for the subsequent time-period, or comparing the set of acceptable data to the medication delivery parameter or intended to be used for the subsequent time-period; and alerting the patient or a user or suggesting another medication delivery parameter in compliance with an acceptable range of the acceptable data.

* * * * *